(12) United States Patent
Kay et al.

(10) Patent No.: US 7,985,739 B2
(45) Date of Patent: Jul. 26, 2011

(54) ENHANCED SLEEPING BEAUTY TRANSPOSON SYSTEM AND METHODS FOR USING THE SAME

(75) Inventors: Mark A. Kay, Los Altos, CA (US); Stephen Yant, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 66 days.

(21) Appl. No.: 10/861,108

(22) Filed: Jun. 3, 2004

(65) Prior Publication Data

US 2005/0003542 A1 Jan. 6, 2005

Related U.S. Application Data

(60) Provisional application No. 60/476,266, filed on Jun. 4, 2003.

(51) Int. Cl.
*A61K 31/70* (2006.01)
*C12N 15/63* (2006.01)
*C07H 21/04* (2006.01)
*G01N 33/00* (2006.01)

(52) U.S. Cl. ....... 514/44; 435/455; 435/320.1; 536/23.2

(58) Field of Classification Search ........................ None
See application file for complete search history.

(56) References Cited

U.S. PATENT DOCUMENTS

| | | | |
|---|---|---|---|
| 6,368,830 B1 * | 4/2002 | Lampe et al. | 435/69.1 |
| 6,489,458 B2 | 12/2002 | Hackett et al. | |
| 6,613,752 B2 * | 9/2003 | Kay et al. | 514/44 |
| 2003/0143740 A1 * | 7/2003 | Wooddell et al. | 435/455 |
| 2004/0077572 A1 * | 4/2004 | Hackett et al. | 514/44 |
| 2005/0112764 A1 * | 5/2005 | Ivics et al. | 435/456 |

FOREIGN PATENT DOCUMENTS

| | | |
|---|---|---|
| WO | WO98/40510 | 9/1998 |
| WO | WO99/25817 | 5/1999 |
| WO | WO 01/30965 | 5/2001 |

OTHER PUBLICATIONS

Zayed et al. Development of hyperactive Sleeping Beauty transposon vectors by mutational analysis. Mol. Ther. 9:292-304, 2004.*
Yant et al. Mutational analysis of the N-terminal DNA-binding domain of Sleeping Beauty Transposase: Critical residues for DNA binding and hyperactivity in mammalian cells. Mol. Cell. Biol. 24:9239-9247, 2004.*
Richardson et al. Gene Repair and Transposon-mediated gene therapy. Stem Cells 20:105-118, 2002.*
Guo et al. Protein tolerance to random amino acid change. PNAS 101:9205-9210, 2004.*
Dawson et al. "Sleeping Beauty Awakes" (1998) *Nature Biotechnology*, 16:20-21.
Ivics et al. "Molecular Reconstruction of Sleeping Beauty, a Tc1-Like Transposon From Fish, and Its Transposition in Human Cells" (1997) *Cell*, 91:501-510.
Ivics et al. "Identification of Functional Domains and Evolution of Tc1-Like Transposable Elements" (1996) *Proc. Natl, Acad. Sci.* 93:5008-5013.
Luo et al. "Chromomsomal Transposition of a Tc1/Mariner-Like Element in Mouse Embryonic Stem Cells" (1998) *Proc. Natl. Acad. Sci*. 95:10769-10773.
Schouten et al, "Transposon Tc1 of the Nematode Caenorhabditis Elegans Jumps in Human Cells" (1998) *Nucleic Acids Research* 26 (12):3013-3017.
Zhang et al. "The Himar1 Mariner Transposase Cloned in a Recombinant Adenovirus Vector is Functional in Mammalian Cells" (1998) *Nucleic Acids Research*, 26(16)3687-3693.
Izsvak et al. "Involvement of a Bifunctional, Paired-Like DNA-Binding Domain and a Transpositional Enhancer in Sleeping Beauty Transposition" (2002) *The Journal of Biological Chemistry* 277(37) 34581-34588.
Cui et al. "Structure-Function Analysis of the Inverted Terminal Repeats of the Sleeping Beauty Transposon" (2002) *J. Mol. Biol.* 318:1221-1235.

* cited by examiner

*Primary Examiner* — Quang Nguyen
(74) *Attorney, Agent, or Firm* — Bozicevic, Field & Francis LLP; Bret E. Field; Elizabeth A. Alcamo

(57) ABSTRACT

Methods and compositions for introducing a nucleic acid into the genome of a cell are provided. In the subject methods, a Sleeping Beauty transposon that includes the nucleic acid is introduced into the cell along with a source of a mutant Sleeping Beauty transposase that provides for enhanced integration as compared to the wild-type Sleeping Beauty transposase having an amino acid sequence as shown in SEQ ID NO:01. Introduction of the mutant Sleeping Beauty Transposase and transposon results in integration of the nucleic acid into the cell genome. Also provided are mutant transposases and transposons, as well as systems and kits thereof, that find use in practicing the subject methods. The subject methods and compositions find use in a variety of different applications.

24 Claims, 18 Drawing Sheets

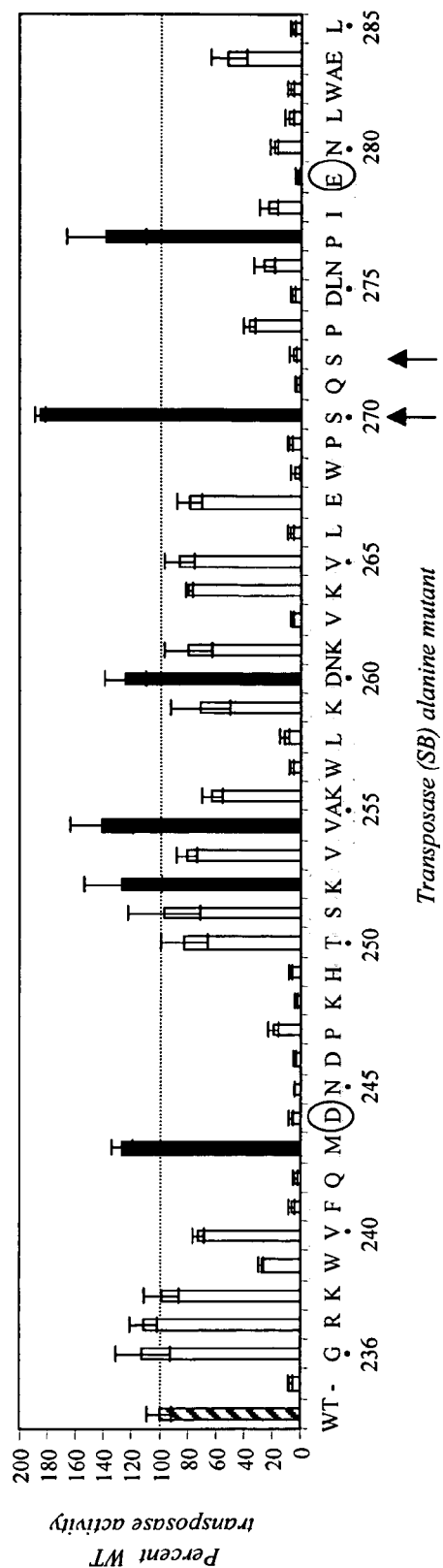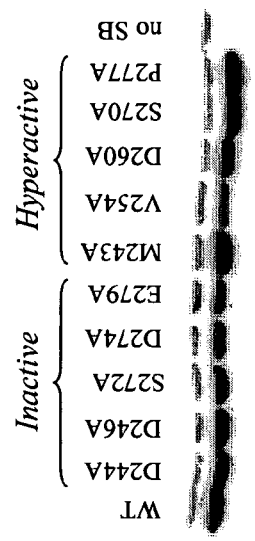
FIG. 12A
FIG. 12B

SEQUENCE LISTING

```
<160> NUMBER OF SEQ ID NOS: 27

<210> SEQ ID NO 1
<211> LENGTH: 340
<212> TYPE: PRT
<213> ORGANISM: salmonid

<400> SEQUENCE: 1

Met Gly Lys Ser Lys Glu Ile Ser Gln Asp Leu Arg Lys Lys Ile Val
 1               5                  10                  15

Asp Leu His Lys Ser Gly Ser Ser Leu Gly Ala Ile Ser Lys Arg Leu
                20                  25                  30

Lys Val Pro Arg Ser Ser Val Gln Thr Ile Val Arg Lys Tyr Lys His
            35                  40                  45

His Gly Thr Thr Gln Pro Ser Tyr Arg Ser Gly Arg Arg Arg Val Leu
        50                  55                  60

Ser Pro Arg Asp Glu Arg Thr Leu Val Arg Lys Val Gln Ile Asn Pro
65                  70                  75                  80

Arg Thr Thr Ala Lys Asp Leu Val Lys Met Leu Glu Glu Thr Gly Thr
                85                  90                  95

Lys Val Ser Ile Ser Thr Val Lys Arg Val Leu Tyr Arg His Asn Leu
            100                 105                 110

Lys Gly Arg Ser Ala Arg Lys Lys Pro Leu Leu Gln Asn Arg His Lys
        115                 120                 125

Lys Ala Arg Leu Arg Phe Ala Thr Ala His Gly Asp Lys Asp Arg Thr
    130                 135                 140

Phe Trp Arg Asn Val Leu Trp Ser Asp Glu Thr Lys Ile Glu Leu Phe
145                 150                 155                 160

Gly His Asn Asp His Arg Tyr Val Trp Arg Lys Lys Gly Glu Ala Cys
                165                 170                 175

Lys Pro Lys Asn Thr Ile Pro Thr Val Lys His Gly Gly Gly Ser Ile
            180                 185                 190

Met Leu Trp Cys Gly Phe Ala Ala Gly Gly Thr Gly Ala Leu His Lys
        195                 200                 205

Ile Asp Gly Ile Met Arg Lys Glu Asn Tyr Val Asp Ile Leu Lys Gln
    210                 215                 220

His Leu Lys Thr Ser Val Arg Lys Leu Lys Leu Gly Arg Lys Trp Val
225                 230                 235                 240

Phe Gln Met Asp Asn Asp Pro Lys His Thr Ser Lys Val Val Ala Lys
                245                 250                 255

Trp Leu Lys Asp Asn Lys Val Lys Val Leu Glu Trp Pro Ser Gln Ser
            260                 265                 270

Pro Asp Leu Asn Pro Ile Glu Asn Leu Trp Ala Glu Leu Lys Lys Arg
        275                 280                 285

Val Arg Ala Arg Arg Pro Thr Asn Leu Thr Gln Leu His Gln Leu Cys
    290                 295                 300
```

-continued

Gln Glu Glu Trp Ala Lys Ile His Pro Thr Tyr Cys Gly Lys Leu Val
305                 310                 315                 320

Glu Gly Tyr Pro Lys Arg Leu Thr Gln Val Lys Gln Phe Lys Gly Asn
            325                 330                 335

Ala Thr Lys Tyr
            340

<210> SEQ ID NO 2
<211> LENGTH: 226
<212> TYPE: DNA
<213> ORGANISM: salmonid

<400> SEQUENCE: 2
agttgaagtc ggaagtttac atacacttaa gttggagtca ttaaaactcg tttttcaact    60
acaccacaaa tttcttgtta acaaacaata gttttggcaa gtcagttagg acatctactt   120
tgtgcatgac acaagtcatt tttccaacaa ttgtttacag acagattatt tcacttataa   180
ttcactgtat cacaattcca gtgggtcaga gtttacata cactaa               226

<210> SEQ ID NO 3
<211> LENGTH: 228
<212> TYPE: DNA
<213> ORGANISM: salmonid

<400> SEQUENCE: 3
ttgagtgtat gttaacttct gacccactgg gaatgtgatg aaagaaataa aagctgaaat    60
gaatcattct ctctactatt attctgatat ttcacattct taaataaag tggtgatcct   120 aactgacctt aagacaggga atctttactc ggattaaatg tcaggaattg tgaaaaagtg   180
agtttaatgt atttggctaa ggtgtatgta aacttccgac ttcaactg             228

<210> SEQ ID NO 4
<211> LENGTH: 29
<212> TYPE: DNA
<213> ORGANISM: salmonid

<400> SEQUENCE: 4
gttcaagtcg gaagtttaca tacacttag                                   29

<210> SEQ ID NO 5
<211> LENGTH: 30
<212> TYPE: DNA
<213> ORGANISM: salmonid

<400> SEQUENCE: 5
cagtgggtca gaagtttaca tacactaagg                                  30

<210> SEQ ID NO 6
<211> LENGTH: 31
<212> TYPE: DNA
<213> ORGANISM: salmonid

<400> SEQUENCE: 6
cagtgggtca gaagttaaca tacactcaat t                                31

<210> SEQ ID NO 7
<211> LENGTH: 30
<212> TYPE: DNA
<213> ORGANISM: salmonid

<400> SEQUENCE: 7
agttgaatcg gaagtttaca tacaccttag                                  30

```
<210> SEQ ID NO 8
<211> LENGTH: 30
<212> TYPE: DNA
<213> ORGANISM: salmonid

<400> SEQUENCE: 8
cagtgagtca gaagtttaca tacacttaag                                     30

<210> SEQ ID NO 9
<211> LENGTH: 8
<212> TYPE: DNA
<213> ORGANISM: salmonid

<400> SEQUENCE: 9 acatacac                                                              8

<210> SEQ ID NO 10
<211> LENGTH: 13
<212> TYPE: DNA
<213> ORGANISM: salmonid

<400> SEQUENCE: 10
gtttacagac aga                                                       13

<210> SEQ ID NO 11
<211> LENGTH: 1023
<212> TYPE: DNA
<213> ORGANISM: salmonid

<400> SEQUENCE: 11
atgggaaaat caaagaaat cagccaagac ctcagaaaaa aaattgtaga cctccacaag      60
tctggttcat ccttgggagc aatttccaaa cgcctgaaag taccacgttc atctgtacaa    120
acaatagtac gcaagtataa acaccatggg accacgcagc cgtcataccg ctcaggaagg    180
agacgcgttc tgtctcctag agatgaacgt actttggtgc gaaaagtgca aatcaatccc    240
agaacaacag caaaggacct tgtgaagatg ctggaggaaa caggtacaaa agtatctata    300
tccacagtaa aacgagtcct atatcgacat aacctgaaag gccgctcagc aaggaagaag    360
ccactgctcc aaaaccgaca taagaaagcc agactacggt ttgcaactgc acatggggac    420
aaagatcgta cttttttggag aaatgtcctc tggtctgatg aaacaaaaat agaactgttt    480
ggccataatg accatcgtta tgtttggagg aagaaggggg aggcttgcaa gccgaagaac    540
accatcccaa ccgtgaagca cgggggtggc agcatcatgt tgtggggtg ctttgctgca     600 ggagggactg gtgcacttca caaaatagat ggcatcatga ggaaggaaaa ttatgtggat    660
atattgaagc aacatctcaa gacatcagtc aggaagttaa agcttggtcg caaatgggtc    720
ttccaaatgg acaatgaccc caagcatact tccaaagttg tggcaaaatg cttaaggac     780 aacaaagtca aggtattgga gtggccatca caaagccctg acctcaatcc tatagaaaat    840
ttgtgggcag aactgaaaaa gcgtgtgcga gcaggaggc ctacaaacct gactcagtta     900
caccagctct gtcaggagga atgggccaaa attcacccaa cttattgtgg gaagcttgtg    960
gaaggctacc cgaaacgttt gacccaagtt aaacaattta aaggcaatgc taccaaatac   1020
tag                                                                1023

<210> SEQ ID NO 12
<211> LENGTH: 30
<212> TYPE: DNA
<213> ORGANISM: salmonid
```

```
<400> SEQUENCE: 12
ctcggatcca tgggaaaatc aaaagaaatc                                      30

<210> SEQ ID NO 13
<211> LENGTH: 29
<212> TYPE: DNA
<213> ORGANISM: salmonid

<400> SEQUENCE: 13
gcagaattct agtatttggt agcattgcc                                       29

<210> SEQ ID NO 14
<211> LENGTH: 31
<212> TYPE: DNA
<213> ORGANISM: salmonid

<400> SEQUENCE: 14
gctctagacc tatacagttg aagtcggaag t                                    31

<210> SEQ ID NO 15
<211> LENGTH: 28
<212> TYPE: DNA
<213> ORGANISM: salmonid

<400> SEQUENCE: 15
gcggatcccc ttgaaataca tccaacgg                                        28

<210> SEQ ID NO 16
<211> LENGTH: 21
<212> TYPE: DNA
<213> ORGANISM: salmonid

<400> SEQUENCE: 16
gatgctgaag atcagttggg t                                               21

<210> SEQ ID NO 17
<211> LENGTH: 21
<212> TYPE: DNA
<213> ORGANISM: salmonid

<400> SEQUENCE: 17
gctagagtaa gtagttcgcc a                                               21

<210> SEQ ID NO 18
<211> LENGTH: 34
<212> TYPE: DNA
<213> ORGANISM: salmonid

<400> SEQUENCE: 18
tacagttgaa gtcggaagtt tacatacact tagg                                 34

<210> SEQ ID NO 19
<211> LENGTH: 32
<212> TYPE: DNA
<213> ORGANISM: salmonid

<400> SEQUENCE: 19
tccagtgggt cagaagttta catacactaa gt                                   32

<210> SEQ ID NO 20
<211> LENGTH: 21
<212> TYPE: DNA
<213> ORGANISM: Artificial Sequence
```

```
<220> FEATURE:
<223> OTHER INFORMATION: Synthetic

<400> SEQUENCE: 20
tcgagctcgg taccctacag t                                              21

<210> SEQ ID NO 21
<211> LENGTH: 21
<212> TYPE: DNA
<213> ORGANISM: Artificial Sequence
<220> FEATURE:
<223> OTHER INFORMATION: Synthetic

<400> SEQUENCE: 21
atggtgactc acacctacag t                                              21

<210> SEQ ID NO 22
<211> LENGTH: 21
<212> TYPE: DNA
<213> ORGANISM: Artificial Sequence
<220> FEATURE:
<223> OTHER INFORMATION: Synthetic

<400> SEQUENCE: 22
ttccagttag aaacatacag t                                              21

<210> SEQ ID NO 23
<211> LENGTH: 21
<212> TYPE: DNA
<213> ORGANISM: Artificial Sequence
<220> FEATURE:
<223> OTHER INFORMATION: Synthetic

<400> SEQUENCE: 23
tgtgtaccaa acatatacag t                                              21

<210> SEQ ID NO 24
<211> LENGTH: 21
<212> TYPE: DNA
<213> ORGANISM: Artificial Sequence
<220> FEATURE:
<223> OTHER INFORMATION: Synthetic

<400> SEQUENCE: 24
agcctgggga tgacctacag t                                              21

<210> SEQ ID NO 25
<211> LENGTH: 3
<212> TYPE: PRT
<213> ORGANISM: Artificial Sequence
<220> FEATURE:
<223> OTHER INFORMATION: Synthetic

<400> SEQUENCE: 25

Asp Asp Glu
 1

<210> SEQ ID NO 26
<211> LENGTH: 97
<212> TYPE: PRT
<213> ORGANISM: Salmonid

<400> SEQUENCE: 26

Gln Asp Leu Arg Lys Lys Ile Val Asp Leu His Lys Ser Gly Ser Ser
 1               5                  10                  15

Leu Gly Ala Ile Ser Lys Arg Leu Lys Val Pro Arg Ser Ser Val Gln
```

-continued

```
                 20                  25                  30
Thr Ile Val Arg Lys Tyr Lys His His Gly Thr Thr Gln Pro Ser Tyr
        35                  40                  45

Arg Ser Gly Arg Arg Arg Val Leu Ser Pro Arg Asp Glu Arg Thr Leu
        50                  55                  60

Val Arg Lys Val Gln Ile Asn Pro Arg Thr Thr Ala Lys Asn Leu Val
 65                  70                  75                  80

Lys Met Leu Glu Glu Thr Gly Thr Lys Val Ser Ile Ser Thr Val Arg
                85                  90                  95

Lys

<210> SEQ ID NO 27
<211> LENGTH: 50
<212> TYPE: PRT
<213> ORGANISM: Salmonid

<400> SEQUENCE: 27

Gly Arg Lys Trp Val Phe Gln Met Asp Asn Asp Pro Lys His Thr Ser
 1               5                  10                  15

Lys Val Val Ala Lys Trp Leu Lys Asp Asn Lys Val Lys Val Leu Glu
                20                  25                  30

Trp Pro Ser Gln Ser Pro Asp Leu Asn Pro Ile Glu Asn Leu Trp Ala
                35                  40                  45

Glu Leu
    50
```

ENHANCED SLEEPING BEAUTY TRANSPOSON SYSTEM AND METHODS FOR USING THE SAME

CROSS-REFERENCE TO RELATED APPLICATIONS

This application claims the priority benefit of U.S. provisional application Ser. No. 60/476,266, filed Jun. 4, 2003, which application is incorporated herein by reference in its entirety.

ACKNOWLEDGMENT

This invention was made with United States Government support under Grant No. AR44012 awarded by the National Institute of Health. The United States Government has certain rights in this invention.

INTRODUCTION

Background of the Invention

The introduction of an exogenous nucleic acid sequence (e.g. DNA) into a cell, a process known as "transformation," plays a major role in a variety of biotechnology and related applications, including research, synthetic and therapeutic applications. Research applications in which transformation plays a critical role include the production of transgenic cells and animals. Synthetic applications in which transformation plays a critical role include the production of peptides and proteins. Therapeutic applications in which transformation plays a key role include gene therapy applications. Because of the prevalent role transformation plays in the above and other applications, a variety of different transformation protocols have been developed.

In many transformation applications, it is desirable to introduce the exogenous DNA in a manner such that it is incorporated into a target cell's genome. One means of providing for genome integration is to employ a vector that is capable of homologous recombination. Techniques that rely on homologous recombination can be disadvantageous in that the necessary homologies may not always exist; the recombination events may be slow, etc. As such, homologous recombination based protocols are not entirely satisfactory.

Accordingly, alternative viral based transformation protocols have been developed, in which a viral vector is employed to introduce exogenous DNA into a cell and then subsequently integrate the introduced DNA into the target cell's genome. Viral based vectors finding use include retroviral vectors, e.g. Moloney murine leukemia viral based vectors. Other viral based vectors that find use include adenovirus derived vectors, HSV derived vectors, sindbis derived vectors, etc. While viral vectors provide for a number of advantages, their use is not optimal in many situations. Disadvantages associated with viral based vectors include immunogenicity, viral based complications, and the like.

The use of transposable elements as genetic tools has contributed significantly to our understanding of biological systems. The Tc1/mariner elements are likely the most widespread transposons in nature, and can transpose in species other than their hosts, making them potential tools for functional genomics in diverse organisms, including vertebrates. However, most naturally occurring Tc1/mariner-like transposons are non-functional due to the accumulation of inactivating mutations. Although no single active element has ever been identified in vertebrates, an active Tc1-like transposon called Sleeping Beauty (SB) was recently reconstructed from pieces of defective fish elements. SB functions in a variety of vertebrate species, including human and mouse cells, and is the most active member of the Tc1/mariner family. Moreover, this element has been applied recently towards gene discovery in the mouse germline, and has been shown to promote stable in vivo delivery of therapeutic genes in somatic tissues of adult mice.

Each end of the SB transposon element contains an IR/DR structure consisting of two short direct repeats (DRs) within a ~230 by imperfect terminal inverted repeat (IR). These direct repeats (~30 bp) serve as core-binding sites for the element-encoded transposase, and the presence of both sites within an individual IR is required for efficient transposition. In addition to the DRs, the left IR of SB contains a half binding site, termed HDR, which acts as a transpositional enhancer-like sequence. Specific binding to the DRs is mediated by an N-terminal, paired-like DNA-binding domain of the transposase. The C-terminal, catalytic domain of the transposase is responsible for all DNA cleavage and strand transfer reactions and is characterized by the presence of a conserved amino acid triad, the DDE (SEQ ID NO:25) motif. This catalytic triad is found in a large group of recombinases, including many eukaryotic and bacterial transposases, retroviral integrases and the RAG1 V(D)J recombinase involved in immunoglobulin gene rearrangements (FIG. 1).

The mobilization of SB elements is a specialized form of DNA recombination and occurs by a cut-and-paste pathway involving a DNA intermediate (FIG. 2). This transposition process involves five distinct stages: (i) association of the transposase with its binding sites within the transposon IRs; (ii) assembly of an active synaptic complex in which the two ends of the element are paired and held together by bound transposase subunits; (iii) transposase-mediated excision of the element from its original donor site, (iv) re-insertion of the excised element into a new target site (TA dinucleotide); and (v) repair of the cellular DNA at both the excision and re-insertion sites.

Relevant Literature

See U.S. Pat. No. 6,489,458. See also published PCT patent applications of interest include: WO 01/30965, WO 98/40510 and WO 99/25817. Also of interest are: Dawson & Finnegan, Nat. Biotechnol. (1998) 16:20-21; Ivics et al., Cell (1997) 91: 501-510; Ivics et al., Proc. Nat'l Acad. Sci. USA (1996) 93:5008-5013; Luo et al., Proc. Nat'l Acad. Sci USA (1998) 95:10769-10773; Schouten et al., Nuc. Acids Res. (1998) 26:3013-3017; Zhang et al., Nuc. Acids Res. (1998) 26:3687-3693. See also Izsvak et al. J. Biochem. (2002)277 (37):34581-8; and Cui et al., J Mol Biol. (2002) 318(5):1221-35.

SUMMARY OF THE INVENTION

Methods and compositions for introducing a nucleic acid into the genome of a cell are provided. In the subject methods, a Sleeping Beauty transposon that includes the nucleic acid is introduced into the cell along with a source of a mutant Sleeping Beauty transposase that provides for enhanced integration as compared to the wild-type Sleeping Beauty transposase having an amino acid sequence as shown in SEQ ID NO:01. Introduction of the mutant Sleeping Beauty Transposase and transposon results in integration of the nucleic acid into the cell genome. Also provided are mutant transposases and transposons, as well as systems and kits thereof,

BRIEF DESCRIPTION OF THE DRAWINGS

FIG. 6A. is a schematic of a new neomycin-marked transposon vector, pT3-Neo, is shown. Compared to the wild-type transposon, pT-Neo, this vector contains an extra transposition enhancer domain (via duplication of the left IR/DR structure) and an extra flanking TA dinucleotide on one side.

FIG. 6B. is a comparison of colony formation with wild-type and improved SB transposase/transposon systems. HeLa cells were co-transfected with either pT-Neo plus pCMV-SB (left) or pT3-Neo plus pCMV-HSB3 (right) and selected for $G418^R$ growth before fixing and staining colonies. A representative dish (1:50 dilution) from triplicate transfections for each experimental condition is shown. HSB3, hyperactive SB mutant 3, containing three different mutations (K13A-K33A-T83A).

FIG. 6C. is a graph showing the transposition frequencies in HeLa cells using improved transposase/transposon components. The yellow bars show the transposition frequency observed with various transposase forms and the improved pT3-Neo vector. Results obtained with the original pT-Neo vector are superimposed in gray for each mutant for comparison. Numbers indicate the estimated transposition frequency in transfected HeLa cells, which was calculated by dividing the average number of $G418^R$ colonies by the total number plated into selection and accounting for an average 33% transfection efficiency. HSB, hyperactive SB mutant.

FIG. 11A. is a schematic overview of experimental approach. C57Bl/6-scid mice (n=4-5 mice per group) were injected via the tail vein with 25 μg of either a standard β-galactosidase-marked transposon (pT-βgeo) or an improved version (pT3-βgeo), together with 1 μg of plasmids encoding nonfunctional transposase (pCMV-mSB), wild-type transposase (pCMV-SB), or two hyperactive transposase mutants (pCMV-HSB-2 and pCMV-HSB-3). Mice were sacrificed at a time when gene expression from episomal transposon forms is no longer detectable (5 weeks) and their livers sectioned and stained for β-galactosidase expression.

FIG. 11B. shows the DNA transposition efficiencies in vivo using wild-type and hyperactive SB transposase/transposon systems. Shown are representative sections from livers isolated 5 weeks after vector administration, together with the average number of X-gal-positive hepatocytes observed under each experimental condition. HSB-2 and HSB-3, hyperactive SB mutants containing K33A/L91A and K13A/K33A/T83A mutations, respectively.

FIGS. 12A-B. demonstrates the effects of amino acid substitutions within SB's catalytic core domain (SEQ ID NO:27) on transposition activity.

FIG. 12A. shows transposition activity of C-terminal domain mutant transposases relative to wild-type. HeLa cells were co-transfected with a plasmid encoding a neomycin-marked transposon (pT/nori) together with plasmids encoding either wild-type transposase (WT), no transposase (−), or a transposase containing an alanine substitution mutation. Two days later, transfected cells were diluted into medium containing G418 and growth selected for two weeks, after which time the G418$^R$ colonies were fixed, stained and counted. The mean G418$^R$ colony counts±st.dev obtained from three independent experiments is shown. Shown are the transpositional efficiencies of 46 single-amino-acid transposase mutants relative to wild-type (stripped column), which was adjusted to 100%. The six individual hyperactive mutants identified in this screen (arbitrarily defined as ≧120% of wild-type activity) are shown as black columns. Numbers indicate SB amino acid positions, circles enclose the highly conserved catalytic aspartate (D) and glutamate (E) residues, and arrows highlight potential phosphorylation sites for ATM family kinases.

FIG. 12B is an immunoblot analysis of wild-type and mutant transposase proteins expressed by plasmid transfection of HeLa cells. Protein extracts were prepared from cells ~40 h post-transfection, subjected to electrophoresis and electroblotting, and the transposase detected with a polyclonal rabbit antibody to the SB protein. Shown are the steady-state levels of five inactive and five hyperactive SB mutants relative to the wild-type transposase.

FIG. 15A. is a schematic overview of three different sized neomycin-marked transposon vectors. Numbers indicate the total size of each transposon in kilobases. SV40, similar virus 40 promoter; Tn5, bacterial promoter; ori, p15A bacterial origin of replication; ApoE/haat, hepatocyte control region from the apolipoprotein E gene; haat; human $\alpha_1$-antitrypsin gene promoter; FIX, human coagulation factor IX cDNA.

FIG. 15B. shows the results of transposition of different sized neomycin-marked transposons in mammalian cells using either wild-type or hyperactive transposases. HeLa cells were transfected with equal molar amounts of the variably-sized transposon vectors together with plasmids encoding no transposase (hatched columns), wild-type SB (white columns), HSB-3 (striped columns) or HSB-5 (black columns). The mean number of G418$^R$ colonies obtained from a 1:50 dilution of the transfected cells is shown for each experimental condition.

FIG. 15C. is the chromosomal insertion site sequences for the 14.1 kb SB element in HeLa cells. Plasmid backbone sequences are shown in lowercase, target site duplications are underlined and transposon sequences are encased within the box (vector: SEQ ID NO:20; integrant 1: SEQ ID NO:21; integrant 2: SEQ ID NO:22; integrant 3: SEQ ID NO:23; and integrant 4: SEQ ID NO:24).

DESCRIPTION OF THE SPECIFIC EMBODIMENTS

Figure 1:
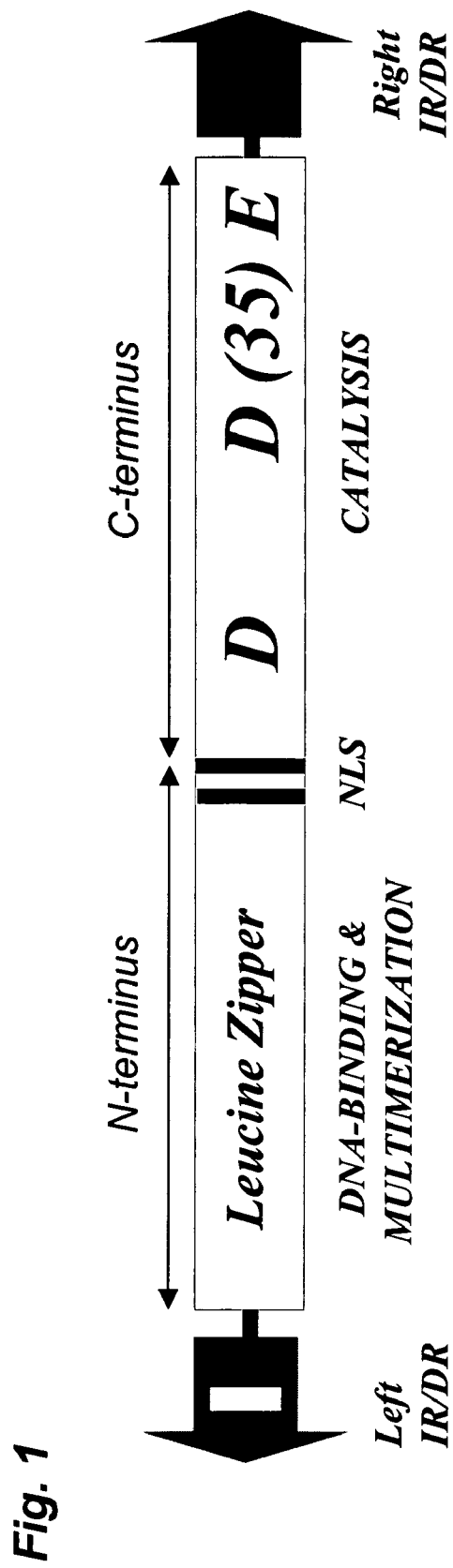
FIG. 1. is an overview of the Sleeping Beauty (SB) transposase/transposon system. The SB transposase contains overlapping N-terminal DNA binding/multimerization domains, a bipartite nuclear localization signal and a C-terminal catalytic domain containing a highly conserved D,D(35)E motif. This protein binds in trans to flanking DNA structures called IR/DRs. The left IR/DR contains an extra transposase binding domain not present in the right IR/DR structure and functions as a transposition enhancer.
Figure 2:
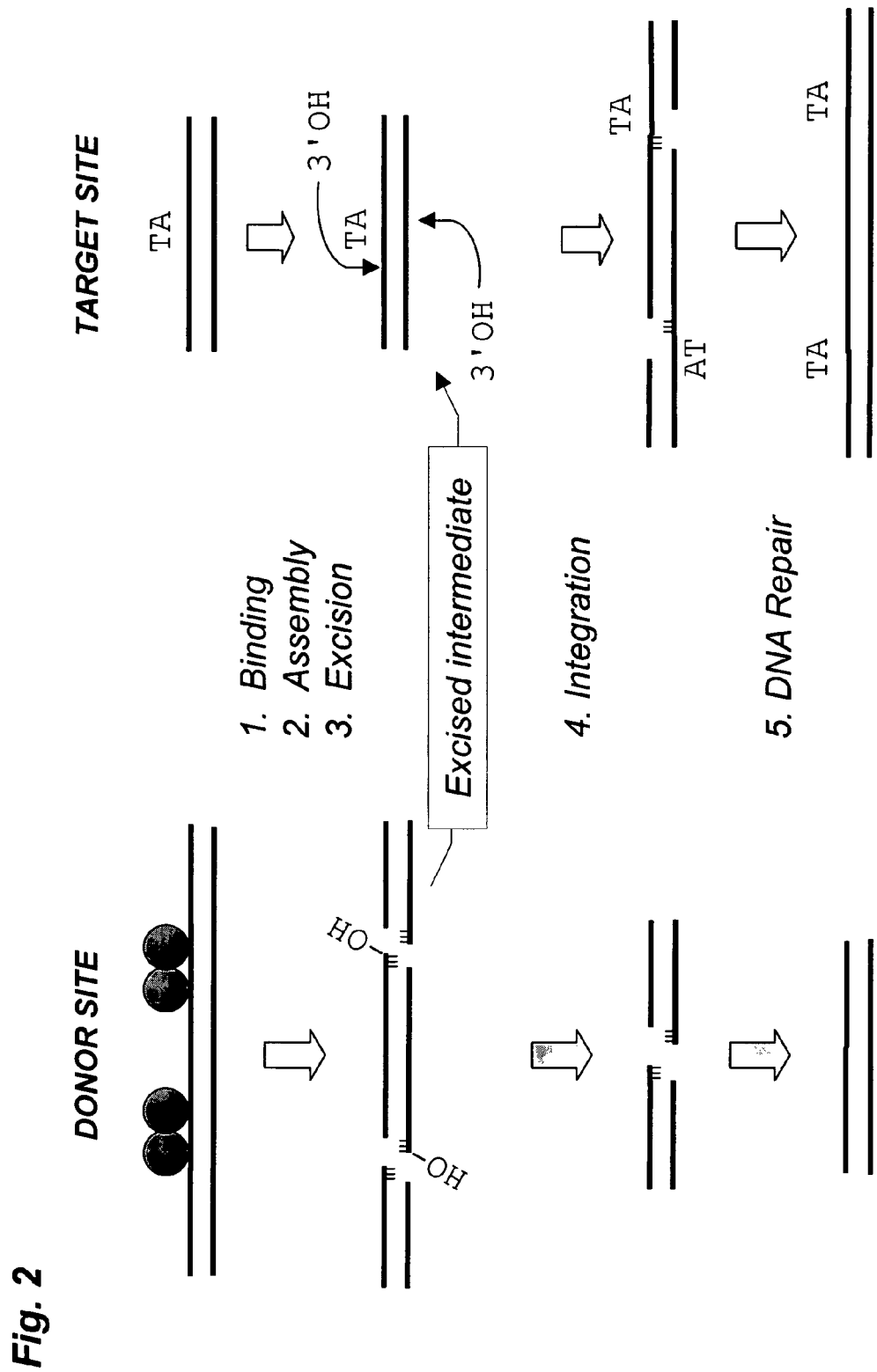
FIG. 2. is a schematic overview of SB-mediated DNA transposition. An SB element is excised by transposase via sequential 3-bp staggered cuts at the ends of the inverted terminal repeats, completely releasing it from its original donor site. This newly excised element then integrates into a TA target site via a series of trans-esterification reactions such that the TA is duplicated at the ends of the element following repair of the single-stranded DNA gaps. Depending on how the double-strand break at the site of excision is repaired, a small transposon footprint will sometimes be left behind.

Methods and compositions for introducing a nucleic acid into the genome of a cell are provided. In the subject methods, a Sleeping Beauty transposon that includes the nucleic acid is introduced info the cell along with a source of a mutant Sleeping Beauty transposase that provides for enhanced integration as compared to the wild-type Sleeping Beauty transposase having an amino acid sequence as shown in SEQ ID NO:01. Introduction of the mutant Sleeping Beauty Transposase and transposon results in integration of the nucleic acid into the cell genome. Also provided are mutant transposases and transposons, as well as systems and kits thereof, that find use in practicing the subject methods. The subject methods and compositions find use in a variety of different applications.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the subject components of the invention that are described in the publications, which components might be used in connection with the presently described invention.

General Introduction

As summarized above, the present invention provides methods of introducing exogenous nucleic acid into the genome of at least one cell, i.e. a target cell. A feature of the subject methods is the use of an enhanced Sleeping Beauty transposon system to integrate the exogenous nucleic acid into the target cell. In further describing the subject invention, the enhanced Sleeping Beauty transposon system will be described first in greater detail, followed by a review of methods of using the subject system and kits for use in practicing the same. In addition, representative utilities in which the subject systems find use are also reviewed.

Enhanced Sleeping Beauty Transposon System

As indicated above, the subject invention provides for an enhanced Sleeping Beauty Transposon system. By enhanced Sleeping Beauty Transposon system is meant a Sleeping Beauty Transposon system that exhibits increased transposon integration as compared to a wild-type Sleeping Beauty Transposon system that is made up of the wild-type Sleeping Beauty transposase, which has an amino acid sequence as shown in SEQ ID NO:01, and a wild-type transposon having inverted repeats having a sequence chosen from SEQ ID NOS. 02 or 03. More specifically, the subject enhanced system exhibits enhanced activity as compared to the wild-type system in a genetic assay that includes co-transfecting HeLa cells with a plasmid encoding a neomycin-marked transposon together with a plasmid encoding either the wild-type or mutagenized transposase under the control of the strong cytomegalovirus (CMV) promoter and then selecting for G418-resistant (G418$^R$) growth for a period of two weeks, as described in greater detail in the Experimental section, with reference to the accompanying figures. The enhanced system of subject invention provides for at least a 2-fold increase in observed signal as compared to wild-type, where the magnitude of enhancement may be at least about 3-fold, including at least about 4-fold, 5-fold, 7-fold, 9-fold, 10-fold or more, e.g., 14-fold.

The enhanced Sleeping Beauty transposon systems employed in the subject methods at least include a Sleeping Beauty transposon and a source of a mutant Sleeping Beauty transposase. Each of these elements is now described in greater detail below.

Sleeping Beauty Transposon

By Sleeping Beauty transposon is meant a nucleic acid that is flanked at either end by inverted repeats which are recognized by an enzyme having Sleeping Beauty transposase activity. By 'recognized' is meant that a Sleeping Beauty transposase is capable of binding to the inverted repeat and then integrating the transposon flanked by the inverted repeat into the genome of the target cell. Representative inverted repeats that may be found in the Sleeping Beauty transposons of the subject methods include those disclosed in WO 98/40510 and WO 99/25817. Of particular interest are inverted repeats that are recognized by the wild type Sleeping Beauty transposase that has an amino acid identity to SEQ ID NO:01, which is:

```
MGKSKEISQD LRKKIVDLHK SGSSLGAISK RLKVPRSSVQ TIVRKYKHHG  (SEQ ID NO: 01)

TTQPSYRSGR RRVLSPRDER TLVRKVQINP RTTAKDLVKM LEETGTKVSI

STVKRVLYRH NLKGRSARKK PLLQNRHKKA RLRFATAHGD KDRTFWRNVL

WSDETKIELF GHNDHRYVWR KKGEACKPKN TIPTVKHGGG SIMLWCGFAA

GGTGALHKID GIMRKENYVD ILKQHLKTSV RKLKLGRKWV FQMDNDPKHT

SKVVAKWLKD NKVKVLEWPS QSPDLNPIEN LWAELKKRVR ARRPTNLTQL

HQLCQEEWAK IHPTYCGKLV EGYPKRLTQV KQFKGNATKY
```

In many embodiments, each inverted repeat of the transposon includes at least one direct repeat. The transposon element is a linear nucleic acid fragment that can be used as a linear fragment or circularlized, for example in a plasmid. In certain embodiments, there are two direct repeats in each inverted repeat sequence. Direct repeat sequences of interest include:

```
The 5' outer repeat:
5'-GTTCAAGTCGGAAGTTTACATACACTTAG-3'   (SEQ ID NO: 04)

The 5' inner repeat:
5'-CAGTGGGTCAGAAGTTTACATACACTAAGG-3'  (SEQ ID NO: 05)

The 3' inner repeat:
5'-CAGTGGGTCAGAAGTTAACATACACTCAATT-   (SEQ ID NO: 06)
3'

The 3' outer repeat:
5'-AGTTGAATCGGAAGTTTACATACACCTTAG-3'  (SEQ ID NO: 07)
```

A consensus sequence of interest is:

```
5'-CA(GT)TG(AG)GTC(AG)GAAGTTTACATACACTTAAG-3'   (SEQ ID NO: 08)
```

In one embodiment, a direct repeat sequence of interest includes at least the following sequence:

```
        ACATACAC            (SEQ ID NO: 09)
```

In certain embodiments, the inverted repeat sequence is:

```
5'-AGTTGAAGTC GGAAGTTTAC ATACACTTAA GTTGGAGTCA TTAAAACTCG (SEQ ID NO: 02)

TTTTTCAACT ACACCACAAA TTTCTTGTTA ACAAACAATA GTTTTGGCAA

GTCAGTTAGG ACATCTACTT TGTGCATGAC ACAAGTCATT TTTCCAACAA

TTGTTTACAG ACAGATTATT TCACTTATAA TTCACTGTAT CACAATTCCA

GTGGGTCAGA AGTTTACATA CACTAA-3'
``` and a second inverted repeat is:

```
5'-TTGAGTGTAT GTTAACTTCT GACCCACTGG GAATGTGATG AAAGAAATAA (SEQ ID NO: 03)

AAGCTGAAAT GAATCATTCT CTCTACTATT ATTCTGATAT TTCACATTCT

TAAAATAAAG TGGTGATCCT AACTGACCTT AAGACAGGGA ATCTTTACTC

GGATTAAATG TCAGGAATTG TGAAAAAGTG AGTTTAATG TATTTGGCTA

AGGTGTATGT AAACTTCCGA CTTCAACTG-3'.
```

Figure 6A:
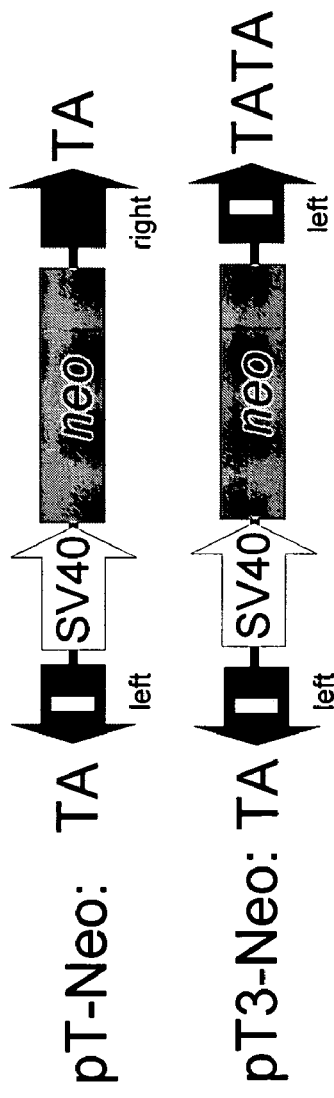
FIGS. 6A-C. Demonstrate the effect of the combined use of an improved transposon (pT3) and hyperactive transposases on the frequency of transgene integration in mammalian cells.

In certain embodiments, the transposon component of the subject systems is characterized by the presence of two additional elements as compared to the above described wild type transposon, where the two additional elements provide for enhanced integration efficiency, as measured using the above described assay, either with the wild-type transposase of SEQ ID NO.: 01 or with a mutant transposase of the present invention, as described in greater detail below. Specifically, the transposon of these embodiments includes an extra tansposon enhancer element (known in the art as an HDR or half direct repeat), e.g., (GTTTACAGACAGA) (SEQ ID NO:10), in addition to the transposon enhancer element found in the wild type left IDR domain. In many embodiments, this additional transposon enhancer element is present in the right flanking IDR domain, e.g., as a duplicate of the wild-type left IDR that has been substituted for the right IDR (as reported in Izsvak et al. J. Biochem. (2002)277(37):34581-8). In addition, the transposon of this embodiment also includes an additional TA dinucleotide adjacent to the right flanking TA dinucleotide (as described in Cui et al., J Mol Biol. (2002) 318(5):1221-35). FIG. 6A provides a diagram of a representative transposon of this embodiment, i.e., pT3, which carries the neo$^r$ coding sequence.

In the subject Sleeping Beauty transposons, the Sleeping Beauty transposase recognized inverted repeats, as described above, flank an insertion nucleic acid, i.e. a nucleic acid that is to be inserted into a target cell genome, as described in greater detail below. The subject transposons may include a wide variety of insertion nucleic acids, where the nucleic acids may include a sequence of bases that is endogenous and/or exogenous to the multicellular organism, where an exogenous sequence is one that is not present in the target cell while an endogenous sequence is one that pre-exists in the target cell prior to insertion. In any event, the nucleic acid of the transposon is exogenous to the target cell, since it originates at a source other than the target cell and is introduced into the cell by the subject methods, as described infra. The nature of the nucleic acid will vary depending the particular protocol being performed. For example, in research applications the exogenous nucleic acid may be a novel gene whose protein product is not well characterized. In such applications, the transposon is employed to stably introduce the gene into the target cell and observe changes in the cell phenotype in order to characterize the gene. Alternatively, in protein synthesis applications, the exogenous nucleic acid encodes a protein of interest which is to be produced by the cell. In yet other embodiments where the transposon is employed, e.g. in gene therapy, the exogenous nucleic acid is a gene having therapeutic activity, i.e. a gene that encodes a product of therapeutic utility. Another way to refer to the insertion nucleic acid of the transposon is as the "inter-inverted repeat domain" of the transposon. The inter inverted repeat domain of the Sleeping Beauty transposon, i.e. that domain or region of the transposon located or positioned between the flanking inverted repeats, may vary greatly in size. The only limitation on the size of the inverted repeat is that the size should not be so great as to inactivate the ability of the transposon system to integrate the transposon into the target genome. The upper and lower limits of the size of this inter inverted repeat domain may readily be determined empirically by those of skill in the art.

A variety of different features may be present in the inter inverted repeat domain of the Sleeping Beauty transposon of the subject systems. In many embodiments, the inter inverted repeat domain is characterized by the presence of at least one transcriptionally active gene. By transcriptionally active gene is meant a coding sequence that is capable of being expressed under intracellular conditions, e.g. a coding sequence in combination with any requisite expression regulatory elements that are required for expression in the intracellular environment of the target cell whose genome is modified by integration of the transposon. As such, the transcriptionally active genes of the subject vectors typically include a stretch of nucleotides or domain, i.e. expression module, that includes a coding sequence of nucleotides in operational combination, i.e. operably linked, with requisite transcriptional mediation or regulatory element(s). Requisite transcriptional mediation elements that may be present in the expression module include promoters, enhancers, termination and polyadenylation signal elements, splicing signal elements, and the like.

Preferably, the expression module includes transcription regulatory elements that provide for expression of the gene in a broad host range. A variety of such combinations are known, where specific transcription regulatory elements include: SV40 elements, as described in Dijkema et al., EMBO J. (1985) 4:761; transcription regulatory elements derived from the LTR of the Rous sarcoma virus, as described in Gorman et al., Proc. Nat'l Acad. Sci USA (1982) 79:6777; transcription regulatory elements derived from the LTR of human cytomegalovirus (CMV), as described in Boshart et al., Cell (1985) 41:521; hsp70promoters, (Levy-Holtzman ,R. and I. Schechter (Biochim. Biophys. Acta (1995) 1263: 96-98) Presnail, J. K. and M. A. Hoy, (Exp. Appl. Acarol. (1994) 18: 301-308)) and the like.

In certain embodiments, the at least one transcriptionally active gene or expression module present in the inter inverted repeat domain acts as a selectable marker. A variety of different genes have been employed as selectable markers, and the particular gene employed in the subject vectors as a selectable marker is chosen primarily as a matter of convenience. Known selectable marker genes include: the thimydine kinase gene, the dihydrofolate reductase gene, the xanthine-guanine phosporibosyl transferase gene, CAD, the adenosine deaminase gene, the asparagine synthetase gene, the antibiotic resistance genes, e.g. tet$^r$, amp$^r$, Cm$^r$ or cat, kan$^r$ or neo$^r$ (aminoglycoside phosphotransferase genes), the hygromycin B phosphotransferase gene, genes whose expression provides for the presence of a detectable product, either directly or indirectly, e.g. β-galactosidase, GFP, and the like.

In many embodiments, the at least one transcriptionally active gene or module encodes a protein that has therapeutic activity for the multicellular organism, where such proteins include, but are not limited to: factor VIII, factor IX, β-globin, low-density lipoprotein receptor, adenosine deaminase, purine nucleoside phosphorylase, sphingomyelinase, glucocerebrosidase, cystic fibrosis transmembrane conductance regulator, α1-antitrypsin, CD-18, ornithine transcarbamylase, argininosuccinate synthetase, phenylalanine hydroxylase, branched-chain α-ketoacid dehydrogenase, fumarylacetoacetate hydrolase, glucose 6-phosphatase, α-L-fucosidase, β-glucuronidase, α-L-iduronidase, galactose 1-phosphate uridyltransferase, interleukins, cytokines, small peptides etc, and the like. The above list of proteins refers to mammalian proteins, and in many embodiments human proteins, where the nucleotide and amino acid sequences of the above proteins are generally known to those of skill in the art.

In addition to the at least one transcriptionally active gene, the inverted repeat domain of the subject transposons also typically include at least one restriction endonuclease recognized site, e.g. restriction site, located between the flanking inverted repeats, which serves as a site for insertion of an exogenous nucleic acid. A variety of restriction sites are known in the art and may be included in the inter inverted repeat domain, where such sites include those recognized by the following restriction enzymes: HindIII, PstI, SalI, AccI, HincII, XbaI, BamHI, SmaI, XmaI, KpnI, SacI, EcoRI, and the like. In many embodiments, the vector includes a polylinker, i.e. a closely arranged series or array of sites recognized by a plurality of different restriction enzymes, such as those listed above.

Mutant Sleeping Beauty Transposase

As mentioned above, many embodiments of the subject enhanced Sleeping Beauty transposon system also include a source of a mutant Sleeping Beauty transposase. The mutant Sleeping Beauty transposase is one that binds to the inverted repeats of the Sleeping Beauty transposon and mediates integration of the transposon into the genome of the target cell with enhanced efficiency as compared to the wild type transposase, i.e., SEQ ID NO:01, e.g., as determined using the integration assay described above.

In some embodiments, the mutant Sleeping Beauty transposase is an N-terminal mutant of the wild type transposase, where by N-terminal mutant is meant that it includes at least one mutation in the N-terminus of the protein, and more specifically in the N-terminal 100 amino acids of the protein. While the one or more mutations may, in the broadest sense, be deletion (where one or more amino acids are deleted) or substitution mutations (where one or more amino acids are substituted with other amino acids, in many embodiments the one or more mutations are substitution mutations, and specifically point mutations, where a single amino acid is replaced by a different amino acid. As indicated above, the mutant transposase may include one or more mutations, where when a plurality of different mutations are present, the number of mutations may be 2, 3, 4 or more (i.e. 99% sequence identity or more with the wild type transposase), including 5, 6, 7, 8 or more (i.e. 98% sequence identity or more with the wild type transposase), such as up to 10 or more (i.e. 97% sequence identity or more with the wild type transposase), but in many embodiments does not exceed about 10.

Where the mutant transposase includes one or more point mutations, specific locations or positions of interest (in terms of residue number starting with the N-terminal residue) are: 13, 33, 34, 64, 69, 72, 83, 90, 91, and 95. In certain embodiments where two or more point mutations are present, specific combinations of interest include but are not limited to those shown in FIG. 5 and FIG. 6C that demonstrate a fold increase over WT in these figures.

Where the mutant includes one or more point mutations, specific mutations of interest include mutations of a wild type residue to alanine. Particular point mutations of interest include, but are not limited to: K13A, K33A, V34A, L64A, E69A, L72A, T83A, M90A, L91A and G95A. Also of interest are substitutions with other amino acids besides alanine.

In other embodiments, the mutant Sleeping Beauty transposase is an C-terminal mutant of the wild type transposase, where by C-terminal mutant is meant that it includes at least one mutation in the C-terminus of the protein, and more specifically in the C-terminal 60 amino acids of the protein. While the one or more mutations may, in the broadest sense, be deletion (where one or more amino acids are deleted) or substitution mutations (where one or more amino acids are substituted with other amino acids, in many embodiments the one or more mutations are substitution mutations, and specifically point mutations, where a single amino acid is replaced by a different amino acid. As indicated above, the mutant transposase may include one or more mutations, where when a plurality of different mutations are present, the number of mutations may be 2, 3, 4 or more (i.e. 99% sequence identity with the wild-type transposase), including 5, 6, 7, 8 or more (i.e. 98% sequence identity with the wild-type transposase), such as up to 10 or more (i.e. 97% sequence identity with the wild-type transposase), but in many embodiments does not exceed about 10.

Where the mutant transposase includes one or more point mutations, specific locations or positions of interest (in terms of residue number starting with the C-terminal residue) are: 243, 252, 254, 260, 69, 270, and 277. In certain embodiments where two or more point mutations are present, specific combinations of interest include but are not limited to the HSB-3 mutant shown in FIG. 13 that demonstrate a fold increase over WT in these figures.

Where the mutant includes one or more point mutations, specific mutations of interest include mutations of a wild type residue to alanine. Particular point mutations of interest include, but are not limited to: M243A, K252A, V254A, D260A, S270A, and P277A. Also of interest are substitutions with other amino acids besides alanine.

In yet other embodiments, the mutant Sleeping Beauty transposase is an N-terminal and C-terminal mutant of the wild type transposase, where by N-terminal and C-terminal mutant is meant that it includes at least one mutation in the N-terminus of the protein, and more specifically in the N-terminal 100 amino acids of the protein, and at least one mutation in the C-terminus of the protein, and more specifically in the C-terminal 60 amino acids of the protein. While the mutations may, in the broadest sense, be deletion (where one or more amino acids are deleted) or substitution mutations (where one or more amino acids are substituted with other amino acids, in many embodiments the mutations are substitution mutations, and specifically point mutations, where a single amino acid is replaced by a different amino acid. As indicated above, the mutant transposase may include two or more mutations, where when a plurality of different mutations are present, the number of mutations may be 3, 4 or more, including 5, 6, 7, 8 or more, such as up to 10 or more, but in many embodiments does not exceed about 10(i.e. about 94% sequence identity with the wild type transposase).

Where the mutant transposase includes point mutations in the N-terminal and C-terminal portions of the protein, specific locations or positions of interest in the N-terminus (in terms of residue number starting with the N-terminal residue) are: 13, 33, 34, 64, 69, 72, 83, 90, 91, and 95, and specific locations or positions of interest in the C-terminus (in terms of residue number starting with the C-terminal residue) are: 243, 252, 254, 260, 69, 270, and 277. In certain embodiments where point mutations are present in the N-terminal and C-terminal portions of the protein, specific combinations of interest include but are not limited to those shown in FIG. 13 that demonstrate a fold increase over WT in these figures.

Where the mutant includes one or more point mutations, specific mutations of interest include mutations of a wild type residue to alanine. Particular point mutations of interest in the N-terminus include, but are not limited to: K13A, K33A, V34A, L64A, E69A, L72A, T83A, M90A, L91A and G95A. Particular point mutations of interest include in the C-terminus include, but are not limited to: M243A, K252A, V254A, D260A, S270A, and P277A. Also of interest are substitutions with other amino acids besides alanine.

The source of Sleeping Beauty transposase of the subject systems may vary. In certain embodiments, the source may be a mutant Sleeping Beauty transposase protein. However, the source may also be a nucleic acid that encodes a mutant Sleeping Beauty transposase, as described above. Where the source is a nucleic acid which encodes a mutant Sleeping Beauty transposase, the nucleic acid encoding the transposase protein is generally part of an expression module, as described above, where the additional elements provide for expression of the transposase as required.

The subject Sleeping Beauty transposon is generally present on a vector which is introduced into the cell, as described in greater detail below. The transposon may be present on a variety of different vectors, where representative vectors include plasmids, viral based vectors, linear DNA molecules and the like, where representative vectors are described infra in greater detail.

In certain embodiments where the source of transposase is a nucleic acid, the Sleeping Beauty transposon and the nucleic acid encoding the transposase are present on separate vectors, e.g. separate plasmids. In certain other embodiments, the transposase encoding domain may be present on the same vector as the transposon, e.g. on the same plasmid. When present on the same vector, the mutant Sleeping Beauty transposase encoding region or domain is located outside the inter inverted repeat flanked domain. In other words, the transposase encoding region is located external to the region flanked by the inverted repeats, i.e. outside the inter inverted repeat domain described supra. Put another way, the transposase encoding region is positioned to the left of the left terminal inverted repeat or the right of the right terminal inverted repeat.

Methods of Preparing the Subject Sleeping Beauty Transposon System

The various elements of the Sleeping Beauty Transposon System employed in the subject methods, e.g. the vector(s) of the subject invention, may be produced by standard methods of restriction enzyme cleavage, ligation and molecular cloning. One protocol for constructing the subject vectors includes the following steps. First, purified nucleic acid fragments containing desired component nucleotide sequences as well as extraneous sequences are cleaved with restriction endonucleases from initial sources, e.g. a vector comprising the Sleeping Beauty transposase gene. Fragments containing the desired nucleotide sequences are then separated from unwanted fragments of different size using conventional separation methods, e.g., by agarose gel electrophoresis. The desired fragments are excised from the gel and ligated together in the appropriate configuration so that a circular nucleic acid or plasmid containing the desired sequences, e.g. sequences corresponding to the various elements of the subject vectors, as described above is produced. Where desired, the circular molecules so constructed are then amplified in a prokaryotic host, e.g. E. coli. The procedures of cleavage, plasmid construction, cell transformation and plasmid production involved in these steps are well known to one skilled in the art and the enzymes required for restriction and ligation are available commercially. (See, for example, R. Wu, Ed., Methods in Enzymology, Vol. 68, Academic Press, N.Y. (1979); T. Maniatis, E. F. Fritsch and J. Sambrook, Molecular Cloning: A Laboratory Manual, Cold Spring Harbor Laboratory Press, Cold Spring Harbor, N.Y. (1982); Catalog 1982-83, New England Biolabs, Inc.; Catalog 1982-83, Bethesda Research Laboratories, Inc. An example of how to construct the vectors employed in the subject methods is provided in the Experimental section, infra. The preparation of a representative Sleeping Beauty transposon system is also disclosed in WO 98/40510 and WO 99/25817.

Methods of Using the Sleeping Beauty Transposon System to Integrate a Nucleic Acid into a Target Cell Genome The subject methods find use in a variety of applications in which it is desired to introduce an exogenous nucleic acid into a target cell, and are particularly of interest where it is desired to express a protein encoded by an expression cassette in a target cell. The subject enhanced Sleeping Beauty Transposon systems may be introduced using either in vitro or in vivo protocols.

As indicated above, the subject systems can be used with a variety of target cells, where target cells are often eukaryotic target cells, including, but not limited to, plant and animal target cells, e.g., insect cells, vertebrate cells, particularly avian cells, e.g., chicken cells, fish, amphibian and reptile cells, mammalian cells, including murine, porcine, ovine, equine, rat, ungulates, dog, cat, monkey, and human cells, and the like.

In the methods of the subject invention, the system components are introduced into the target cell. Any convenient protocol may be employed, where the protocol may provide for in vitro or in vivo introduction of the system components into the target cell, depending on the location of the target cell. For example, where the target cell is an isolated cell, the system may be introduced directly into the cell under cell culture conditions permissive of viability of the target cell, e.g., by using standard transformation techniques. Such techniques include, but are not necessarily limited to: viral infection, transformation, conjugation, protoplast fusion, electroporation, particle gun technology, calcium phosphate precipitation, direct microinjection, viral vector delivery, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons,1995.

Alternatively, where the target cell or cells are part of a multicellular organism, the subject system may be administered to the organism or host in a manner such that the targeting construct is able to enter the target cell(s), e.g., via an in vivo or ex vivo protocol. By "in vivo," it is meant in the target construct is administered to a living body of an animal. By "ex vivo" it is meant that cells or organs are modified outside of the body. Such cells or organs are typically returned to a living body. Methods for the administration of nucleic acid constructs are well known in the art. Nucleic acid constructs can be delivered with cationic lipids (Goddard, et al, Gene Therapy, 4:1231-1236, 1997; Gorman, et al, Gene Therapy 4:983-992, 1997; Chadwick, et al, Gene Therapy 4:937-942, 1997; Gokhale, et al, Gene Therapy 4:1289-1299, 1997; Gao, and Huang, Gene Therapy 2:710-722, 1995), using viral vectors (Monahan, et al, Gene Therapy 4:40-49, 1997; Onodera, et al, Blood 91:30-36, 1998), by uptake of "naked DNA", and the like. Techniques well known in the art for the transformation of cells (see discussion above) can be used for the ex vivo administration of nucleic acid constructs. The exact formulation, route of administration and dosage can be chosen empirically. (See e.g. Fingl et al., 1975, in "The Pharmacological Basis of Therapeutics", Ch. 1 p1).

As such, in certain embodiments the vector or vectors comprising the various elements of the enhanced Sleeping Beauty transposon system, e.g. plasmids, are administered to a multicellular organism that includes the target cell, i.e. the cell into which integration of the nucleic acid of the transposon is desired. By multicellular organism is meant an organism that is not a single celled organism. Multicellular organisms of interest include plants and animals, where animals are of particular interest. Animals of interest include vertebrates, where the vertebrate is a mammal in many embodiments. Mammals of interest include; rodents, e.g. mice, rats; livestock, e.g. pigs, horses, cows, etc., pets, e.g. dogs, cats; and primates, e.g. humans. As the subject methods involve administration of the transposon system directly to the multicellular organism, they are in vivo methods of integrating the exogenous nucleic acid into the target cell.

The route of administration of the Sleeping Beauty transposon system to the multicellular organism depends on several parameters, including: the nature of the vectors that carry the system components, the nature of the delivery vehicle, the nature of the multicellular organism, and the like, where a common feature of the mode of administration is that it provides for in vivo delivery of the transposon system components to the target cell(s). In certain embodiments, linear or circularized DNA, e.g. a plasmid, is employed as the vector for delivery of the transposon system to the target cell. In such embodiments, the plasmid may be administered in an aqueous delivery vehicle, e.g. a saline solution. Alternatively, an agent that modulates the distribution of the vector in the multicellular organism may be employed. For example, where the vectors comprising the subject system components are plasmid vectors, lipid based, e.g. liposome, vehicles may be employed, where the lipid based vehicle may be targeted to a specific cell type for cell or tissue specific delivery of the vector. Patents disclosing such methods include: U.S. Pat. Nos. 5,877,302; 5,840,710; 5,830,430; and 5,827,703, the disclosures of which are herein incorporated by reference. Alternatively, polylysine based peptides may be employed as carriers, which may or may not be modified with targeting moieties, and the like. (Brooks, A. I., et al. 1998, J. Neurosci. Methods V. 80 p: 137-47; Muramatsu, T., Nakamura, A., and H. M. Park 1998, Int. J. Mol. Med. V. 1 p: 55-62). In yet other embodiments, the system components may be incorporated onto viral vectors, such as adenovirus derived vectors, sindbis virus derived vectors, retroviral derived vectors, etc. hybrid vectors, and the like. The above vectors and delivery vehicles are merely representative. Any vector/delivery vehicle combination may be employed, so long as it provides for in vivo administration of the transposon system to the multicellular organism and target cell.

Because of the multitude of different types of vectors and delivery vehicles that may be employed, administration may be by a number of different routes, where representative routes of administration include: oral, topical, intraarterial, intravenous, intraperitoneal, intramuscular, etc. The particular mode of administration depends, at least in part, on the nature of the delivery vehicle employed for the vectors which harbor the Sleeping Beauty transposons system. In many embodiments, the vector or vectors harboring the Sleeping Beauty transposase system are administered intravascularly, e.g. intraarterially or intravenously, employing an aqueous based delivery vehicle, e.g. a saline solution.

In practicing the subject methods, the elements of the Sleeping Beauty transposase system, e.g. the Sleeping Beauty transposon and the Sleeping Beauty transposase source, are introduced into a target cell of the multicellular organism under conditions sufficient for excision of the inverted repeat flanked nucleic acid from the vector carrying the transposon and subsequent integration of the excised nucleic acid into the genome of the target cell. As the transposon is introduced into the cell "under conditions sufficient for excision and integration to occur," the subject method further includes a step of ensuring that the requisite Sleeping Beauty transposase activity is present in the target cell along with the introduced transposon. Depending on the structure of the transposon vector itself, i.e. whether or not the vector includes a region encoding a product having Sleeping Beauty transposase activity, the method may further include introducing a second vector into the target cell which encodes the requisite transposase activity, where this step also includes an in vivo administration step.

The amount of vector nucleic acid comprising the transposon element, and in many embodiments the amount of vector nucleic acid encoding the transposase, that is introduced into the cell is sufficient to provide for the desired excision and insertion of the transposon nucleic acid into the target cell genome. As such, the amount of vector nucleic acid introduced should provide for a sufficient amount of transposase activity and a sufficient copy number of the nucleic acid that is desired to be inserted into the target cell. The amount of vector nucleic acid that is introduced into the target cell varies depending on the efficiency of the particular introduction protocol that is employed, e.g. the particular in vivo administration protocol that is employed.

For in vivo administration applications, the particular dosage of each component of the system that is administered to the multicellular organism varies depending on the nature of the transposon nucleic acid, e.g. the nature of the expression module and gene, the nature of the vector on which the component elements are present, the nature of the delivery vehicle and the like. Dosages can readily be determined empirically by those of skill in the art. For example, in mice where the Sleeping Beauty Transposase system components are present on separate plasmids which are intravenously administered to a mammal in a saline solution vehicle, the amount of transposon plasmid that is administered in many embodiments typically ranges from about 0.5 to 40 and is typically about 25 µg, while the amount of Sleeping Beauty transposase encoding plasmid that is administered typically ranges from about 0.5 to 25 and is usually about 1 µg.

Once the vector DNA has entered the target cell in combination with the requisite transposase, the nucleic acid region of the vector that is flanked by inverted repeats, i.e. the vector nucleic acid positioned between the Sleeping Beauty transposase recognized inverted repeats, is excised from the vector via the provided transposase and inserted into the genome of the targeted cell. As such, introduction of the vector DNA into the target cell is followed by subsequent transposase mediated excision and insertion of the exogenous nucleic acid carried by the vector into the genome of the targeted cell.

The subject methods may be used to integrate nucleic acids of various sizes into the target cell genome. Generally, the size of DNA that is inserted into a target cell genome using the subject methods ranges from about 0.5 kb to 10.0 kb, usually from about 1.0 kb to about 8.0 kb.

The subject methods result in stable integration of the nucleic acid into the target cell genome. By stable integration is meant that the nucleic acid remains present in the target cell genome for more than a transient period of time, and is passed on a part of the chromosomal genetic material to the progeny of the target cell.

Utility

The subject methods of stable integration of nucleic acids into the genome of a target cell find use in a variety of applications in which the stable integration of a nucleic acid into a target cell genome is desired. Applications in which the subject vectors and methods find use include: research applications, polypeptide synthesis applications and therapeutic applications. Each of these representative categories of applications is described separately below in greater detail.

Research Applications

Examples of research applications in which the subject methods of nucleic acid integration find use include applications designed to characterize a particular gene. In such applications, the subject transposon system is employed to insert a gene of interest into a target cell and the resultant effect of the inserted gene on the cell's phenotype is observed. In this manner, information about the gene's activity and the nature of the product encoded thereby can be deduced. The subject transposon systems can also be employed to identify and define DNA sequences that control gene expression, e.g. in a temporal (e.g. certain developmental stage) or spatial (e.g. particular cell or tissue type) manner. In such assays, the subject transposons are employed to stably integrate into the genome of a target cell a selectable marker gene, e.g. antibiotic resistance, LacZ, etc., where the transposon lacks a sufficient promoter for the marker gene such that the marker is not significantly expressed, if at all, unless it is underneath an endogenous promoter element. If the marker gene is inserted into the target cell genome in sufficient relationship to an endogenous promoter sequence, it will be expressed. From the resultant expression profile of the marker gene, the endogenous promoter that is mediating its expression can then be characterized.

The subject methods can also be used to study integration mutants, where a gene of interest is inserted randomly into the genome and the effects of this random insertion on the targeted cell phenotype are observed. One can also employ the subject methods to produce models in which overexpression and/or misexpression of a gene of interest is produced in a cell and the effects of this mutant expression pattern are observed. One can also use the subject methods to readily clone genes introduced into a host cell via insertional mutagenesis that yields phenotypes and/or expression patterns of interest. In such applications, the subject transposon systems are employed to generate insertional mutants through random integration of DNA. The phenotype and/or expression pattern of the resultant mutant is then assayed using any convenient protocol. In those mutants of interest, cloning of the DNA associated with the phenotype and/or expression pattern of interest is readily accomplished through use of the inverted repeats of the transposon.

Polypeptide Synthesis Applications

In addition to the above research applications, the subject methods also find use in the synthesis of polypeptides, e.g. proteins of interest. In such applications, a transposon that includes a gene encoding the polypeptide of interest in combination with requisite and/or desired expression regulatory sequences, e.g. promoters, etc., (i.e. an expression module) is introduced into the target cell, via in vivo administration to the multicellular organism in which the target cell resides, that is to serve as an expression host for expression of the polypeptide. Following in vivo administration and subsequent stable integration into the target cell genome, the multicellular organism, and targeted host cell present therein, is then maintained under conditions sufficient for expression of the integrated gene. The expressed protein is then harvested, and purified where desired, using any convenient protocol.

As such, the subject methods provide a means for at least enhancing the amount of a protein of interest in a multicellular organism. The term 'at least enhance' includes situations where the methods are employed to increase the amount of a protein in a multicellular organism where a certain initial amount of protein is present prior to in vivo administration of the transposon system. The term 'at least enhance' also includes those situations in which the multicellular organism includes substantially none of the protein prior to administration of the transposon system. As the subject methods find use in at least enhancing the amount of a protein present in a multicellular organism, they find use in a variety of different applications, including agricultural applications, pharmaceutical preparation applications, and the like, as well as therapeutic applications, described in greater detail infra.

Therapeutic Applications

The subject methods also find use in therapeutic applications, in which the transposon systems are employed to stably integrate a therapeutic nucleic acid, e.g. gene, into the genome of a target cell, i.e. gene therapy applications. The subject transposon systems may be used to deliver a wide variety of therapeutic nucleic acids. Therapeutic nucleic acids of interest include genes that replace defective genes in the target host cell, such as those responsible for genetic defect based diseased conditions; genes which have therapeutic utility in the treatment of cancer; and the like. Specific therapeutic genes for use in the treatment of genetic defect based disease conditions include genes encoding the following products: factor VII, factor IX, β-globin, low-density lipoprotein receptor, adenosine deaminase, purine nucleoside phosphorylase, sphingomyelinase, glucocerebrosidase, cystic fibrosis transmembrane conductance regulator, α1-antitrypsin, CD-18, ornithine transcarbamylase, argininosuccinate synthetase, phenylalanine hydroxylase, branched-chain α-ketoacid dehydrogenase, fumarylacetoacetate hydrolase, glucose 6-phosphatase, α-L-fucosidase, β-glucuronidase, α-L-iduronidase, galactose 1-phosphate uridyltransferase, interleukins, cytokines, small peptides etc, and the like. The above list of proteins refers to mammalian proteins, and in many embodiments human proteins, where the nucleotide and amino acid sequences of the above proteins are generally known to those of skill in the art. Cancer therapeutic genes that may be delivered via the subject methods include: genes that enhance the antitumor activity of lymphocytes, genes whose expression product enhances the immunogenicity of tumor cells, tumor suppressor genes, toxin genes, suicide genes, multiple-drug resistance genes, antisense sequences, and the like. The subject methods can be used to not only introduce a therapeutic gene of interest, but also any expression regulatory elements, such as promoters, and the like, which may be desired so as to obtain the desired temporal and spatial expression of the therapeutic gene.

In certain embodiments the subject methods may be used for in vivo gene therapy applications. By in vivo gene therapy applications is meant that the target cell or cells in which expression of the therapeutic gene is desired are not removed from the host prior to contact with the transposon system. In contrast, vectors that include the transposon system are administered directly to the multicellular organism and are taken up by the target cells, following which integration of the gene into the target cell genome occurs.

In yet other embodiments, the methods are not methods of gene therapy.

Additional representative applications in which the subject systems find use include those described in U.S. Pat. No. 6,489,458, the disclosure of which is herein incorporated by reference (specifically col. 16, line 9 to Col. 21, line 2).

Kits

Also provided by the subject invention are kits for use in practicing the subject methods of nucleic acid delivery to target cells. The subject kits generally include one or more components of the subject enhanced Sleeping Beauty Transposase systems, which components may be present in an aqueous medium. The subject kits may further include an aqueous delivery vehicle, e.g. a buffered saline solution, etc. In addition, the kits may include one or more restriction endonucleases for use in transferring a nucleic acid into the vector components of the kits. In the subject kits, the above components may be combined into a single aqueous composition for delivery into the host or separate as different or disparate compositions, e.g., in separate containers. Optionally, the kit may further include a vascular delivery means for delivering the aqueous composition to the host, e.g. a syringe etc., where the delivery means may or may not be pre-loaded with the aqueous composition.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g. a piece or pieces of paper on which the information is printed, in the packaging of the kit, in a package insert, etc. Yet another means would be a computer readable medium, e.g. diskette, CD, etc., on which the information has been recorded. Yet another means that may be present is a website address which may be used via the internet to access the information at a removed site. Any convenient means may be present in the kits.

Additional Features

As indicated above, the mutant transposase protein of the present invention can be introduced into the cell as ribonucleic acid, including mRNA; as DNA present in the cell as extrachromosomal DNA including, but not limited to, episomal DNA, as plasmid DNA, or as viral nucleic acid. Further, DNA encoding the transposase can be stably integrated into the genome of the cell for constitutive or inducible expression. Where the transposase is introduced into the cell as nucleic acid, the transposase encoding sequence is preferably operably linked to a promoter. There are a variety of promoters that could be used including, but not limited to, constitutive promoters, tissue-specific promoters, inducible promoters, and the like. Promoters are regulatory signals that bind RNA polymerase in a cell to initiate transcription of a downstream (3' direction) coding sequence. A DNA sequence is operably linked to an expression-control sequence, such as a promoter when the expression control sequence controls and regulates the transcription and translation of that DNA sequence. The term "operably linked" includes having an appropriate start signal (e.g., ATG) in front of the DNA sequence to be expressed and maintaining the correct reading frame to permit expression of the DNA sequence under the control of the expression control sequence to yield production of the desired protein product.

A nucleic acid sequence encoding the wild type Sleeping Beauty Transposase is:

```
ATGGGAAAAT CAAAAGAAAT CAGCCAAGAC CTCAGAAAAA AAATTGTAGA CCTCCACAAG    60  (SEQ ID NO:11)

TCTGGTTCAT CCTTGGGAGC AATTTCCAAA CGCCTGAAAG TACCACGTTC ATCTGTACAA   120

ACAATAGTAC GCAAGTATAA ACACCATGGG ACCACGCAGC CGTCATACCG CTCAGGAAGG   180
```

-continued

```
AGACGCGTTC TGTCTCCTAG AGATGAACGT ACTTTGGTGC GAAAAGTGCA AATCAATCCC    240

AGAACAACAG CAAAGGACCT TGTGAAGATG CTGGAGGAAA CAGGTACAAA AGTATCTATA    300

TCCACAGTAA AACGAGTCCT ATATCGACAT AACCTGAAAG GCCGCTCAGC AAGGAAGAAG    360

CCACTGCTCC AAAACCGACA TAAGAAAGCC AGACTACGGT TTGCAACTGC ACATGGGAC     420

AAAGATCGTA CTTTTTGGAG AAATGTCCTC TGGTCTGATG AAACAAAAAT AGAACTGTTT    480

GGCCATAATG ACCATCGTTA TGTTTGGAGG AAGAAGGGGG AGGCTTGCAA GCCGAAGAAC    540

ACCATCCCAA CCGTGAAGCA CGGGGGTGGC AGCATCATGT TGTGGGGGTG CTTTGCTGCA    600

GGAGGGACTG GTGCACTTCA CAAAATAGAT GGCATCATGA GGAAGGAAAA TTATGTGGAT    660

ATATTGAAGC AACATCTCAA GACATGAGTC AGGAAGTTAA AGCTTGGTCG CAAATGGGTC    720

TTCCAAATGG ACAATGACCC CAAGCATACT TCCAAAGTTG TGGCAAAATG GCTTAAGGAC    780

AACAAAGTCA AGGTATTGGA GTGGCCATCA CAAAGCCCTG ACCTCAATCC TATAGAAAAT    840

TTGTGGGCAG AACTGAAAAA GCGTGTGCGA GCAAGGAGGC CTACAAACCT GACTCAGTTA    900

CACCAGCTCT GTCAGGAGGA ATGGGCCAAA ATTCACCCAA CTTATTGTGG GAAGCTTGTG    960

GAAGGCTACC CGAAACGTTT GACCCAAGTT AAACAATTTA AAGGCAATGC TACCAAATAC   1020

TAG
```

Nucleic acids according to the present invention are modified from the above wild type sequence to encode for the desired mutant transposases, as described above. As is known in the art, a given mutant transposase may coded for by a number of different nucleic acid sequences as a result of the degeneracy of the three letter codons used to specify a particular amino acid. For example, it is well known in the art that the following RNA codons (and therefore, the corresponding DNA codons, with a T substituted for a U) can be used interchangeably to code for each specific amino acid:

| | |
|---|---|
| Phenylalanine (Phe or F) | UUU or UUC |
| Leucine (Leu or L) | UUA, UUG, CUU, CUC, CUA or CUG |
| Isoleucine (Ile or I) | AUU, AUG or AUA |
| Methionine (Met or M) | AUG |
| Valine (Val or V) | GUU, GUC, GUA, GUG |
| Serine (Ser or S) | UCU, UCC, UCA, UCG, AGU, AGC |
| Proline (Pro or P) | CCU, CCC, CCA, CCG |
| Threonine (Thr or T) | ACU, ACC, ACA, ACG |
| Alanine (Ala or A) | GCU, GCG, GCA, GCC |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAG |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU, CGC, CGA, CGG, AGA, AGC |
| Glycine (Gly or C) | GGU or GGC or GGA or GGG |
| Termination codon | UAA, UAG or UGA |

Further, a particular DNA sequence can be modified to employ the codons preferred for a particular cell type. For example, the preferred codon usage for E. coli is known, as are preferred codon usages for animals and humans. These changes are known to those of ordinary skill in the art and are therefore considered part of this invention.

Also contemplated in this invention are antibodies directed to a mutant Sleeping Beauty transposase of this invention. An "antibody" for purposes of this invention is any immunoglobulin, including antibodies and fragments thereof that specifically binds to the subject transposase. The antibodies can be polyclonal, monoclonal and chimeric antibodies. Various methods are known in the art that can be used for the production of polyclonal or monoclonal antibodies to the subject transposases. See, for example, Antibodies: A Laboratory Manual, Harlow and Lane, eds., Cold Spring Harbor Laboratory Press: Cold Spring Harbor, N.Y., 1988).

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

The following methods and materials are used in the examples below.

Recombinant DNA and SB Mutagenesis

To express WT SB from a CMV promoter, we PCR-amplified the SB gene from pCMV-SB (Ivics et al., 1999, Cell 91:501-510) using the following primers

```
5'-                                         (SEQ ID NO: 12)
CTCGGATCCATGGGAAAATCAAAAGAAATC-
3'

5'-                                         (SEQ ID NO: 13)
GCAGAATTCTAGTATTTGGTAGCATTGCC-              (SEQ ID NO: 13)
3'
``` and inserted the amplification product into the null vector pc-N (Yant et al., 2000, Nature Genetics 25:35-41) by BamHI/EcoRI ligation. Alanine substitutions were introduced into the SB gene using mutagenic PCR primers, and each mutation was confirmed by DNA sequencing. For in vitro protein production, the N123 portion of the various SB mutants was isolated by PCR and cloned into the EcoRI/BamHI sites of pGADT7 (Clontech, Palo Alto, Calif.). To generate pT3/MCS and pT3/nori, we PCR-amplified the left IR/DR structure from pT/nori using the following primers

5'-GCTCTAGACCTATACAGTTGAAGTCGGAAGT-3'     (SEQ ID NO: 14)

5'-GCGGATCCCCTTGAAATACATCCAACGG-3'     (SEQ ID NO: 15)

and inserted it into pT/MCS (Yant et al., 2000) and pT/nori by BamHI-XbaI ligation. The pT3/βgeo vector was made by inserting the βgeo cassette from pT/βgeo into pT3/MCS by XhoI ligation.

Transposition Assay, Immunobloting, and Southern Blot Analysis

HeLa cells ($5 \times 10^5$) were transfected with pT/nori or pT3/nori, together with pc-N, pc-SB10, or plasmids encoding individual SB mutants. In some cases, cells were harvested 40 hours later, lysed in the presence of a complete protease inhibitor mix (Boehringer), and analyzed by immunoblotting with a rabbit polyclonal antibody to SB transposase (Geurts et al., 2003, J. Biol. Chem. 273:7367-7374). To measure transpositional activity, transfected cells were trypsinized 2 days after transfection, diluted into DMEM containing 600 μg/ml G418, and growth-selected for a period of 2 weeks. G418 resistant colonies were counted to determine the amount of SB-mediated integration relative to wild-type, which was adjusted to 100%. In some cases, G418 resistant colonies were isolated, amplified and used to prepare genomic DNA for Southern blot analysis using a radiolabeled neo probe (Yant et al., 2003, Mol. Cell. Biol. 23:8505-8518).

Electrophoretic Mobility Shift Assay (EMSA)

Truncated (N123) derivatives of wild-type and mutant SB proteins were generated using the TNT T7 coupled reticulocyte lysate system (Promega) according to the manufacturer's instructions. Double-stranded oligonucleotides corresponding to the outer and inner direct repeats (DRs) from SB's left inverted repeat (IR) were end-labeled using [γ-$^{32}$P]ATP and PNK. Complexes were formed in a 10 μl volume containing 10 fmol labeled oligonucleotide, 6 μl of in vitro translation product, 1 μg poly(dI)(dC), and binding buffer as previously described (Ivics et al., 1997). For competitions, increasing amounts (1-500 nM) of the corresponding unlabeled oligonucleotide was added to the reaction. After a 90 minute incubation at 22° C., 5 μl of loading dye was added and each sample was resolved on a 5% polyacrylamide gel for 2-3 hours at 120 volts. Binding affinities were determined by measuring the ratio of bound vs. free radiolabeled probe using a Phosphorimager, and normalized according to the amount bound in the absence of cold competitor minus the amount bound at the highest competitor concentration.

Donor Cleavage Assay

HeLa cells ($5 \times 10^5$) were transfected with pT/nori together with either pc-N or plasmids encoding transposase. DNA was then isolated 30 hours later by Hirt method and assayed for SB-element donor DNA cleavage using a previously described PCR-based assay (Yant et al., 2003). Potential DNA variations between samples were controlled by amplifying a portion of the plasmid backbone using the following primers

5'-GATGCTGAAGATCAGTTGGGT-3'     (SEQ ID NO: 16)

5'-GCTAGAGTAAGTAGTTCGCCA-3'.    (SEQ ID NO: 17)

PCR products were analyzed on an ethidium bromide gel and quantified using a densitometer. Amounts of excision and repair products generated under each experimental condition were normalized for total DNA content, and further estimated by limiting dilution PCR Chromosomal Transposition Assay Three reporter cell lines were generated (15-2, 15-8, and 15-11), each containing a single integrated copy of a neomycin expression cassette disrupted by a hygromycin-marked transposon (Yant et al., 2003). These cell lines were screened for sensitivity to the drug G418, and transiently transfected ($2 \times 10^6$) with 20 μg pc-N, pc-SB10, or pc-HSB3 to promote chromosomal transposition. Cells were growth-selected for 3 weeks in DMEM containing 600 μg/ml G418, at which time, G418 resistant colonies were counted.

Animal Studies

Eight-week-old C57Bl/6-scid mice were obtained from Jackson Laboratory and treated according to the NIH Guidelines for Animal Care and the Guidelines of Stanford University. Plasmid DNAs were delivered to mice by hydrodynamics-based transfection as previously described (Liu et al., 1999, Gene Ther., 6:1258-1266; Zhang et al., 1999, Hum. Gene Ther., 10:1735-1737). Frozen mouse liver tissue was analyzed for â-galactosidase expression by immunohistochemistry (Yant et al., 2000).

The following examples are offered by way of illustration and not by way of limitation.

A. Directed Mutagenesis of the Sleeping Beauty (SB) Transposase N-terminal Domain.

To determine whether transposase integration activity could be improved through directed protein evolution, we mutagenized residues 9-105 of the SB transposase by PCR-mediated alanine substitution and tested for enhanced transposition activity using the HeLa cell transposition assay. This genetic assay involves co-transfecting HeLa cells with a plasmid encoding a neomycin-marked transposon together with a plasmid encoding either the wild-type or mutagenized transposase under the control of the strong cytomegalovirus (CMV) promoter and then selecting for transposon integration events by diluting transfected cells into DMEM media containing G418 (600 μg/ml) and selecting for G418-resistant (G418$^R$) growth for a period of two weeks. At this point, the remaining cells stably expressing the transposon-encoded neomycin gene were fixed, stained with methylene blue and counted in order to determine the mean number of integration events under each experimental condition. In all experiments, cells transfected with the wild-type transposon and transposase vector were performed at least five and all the number of G418$^R$ colonies formed with each mutant transposase was compared relative to the integration (i.e., G418$^R$ colony-forming ability) of the wild-type SB transposase.

Figure 3:
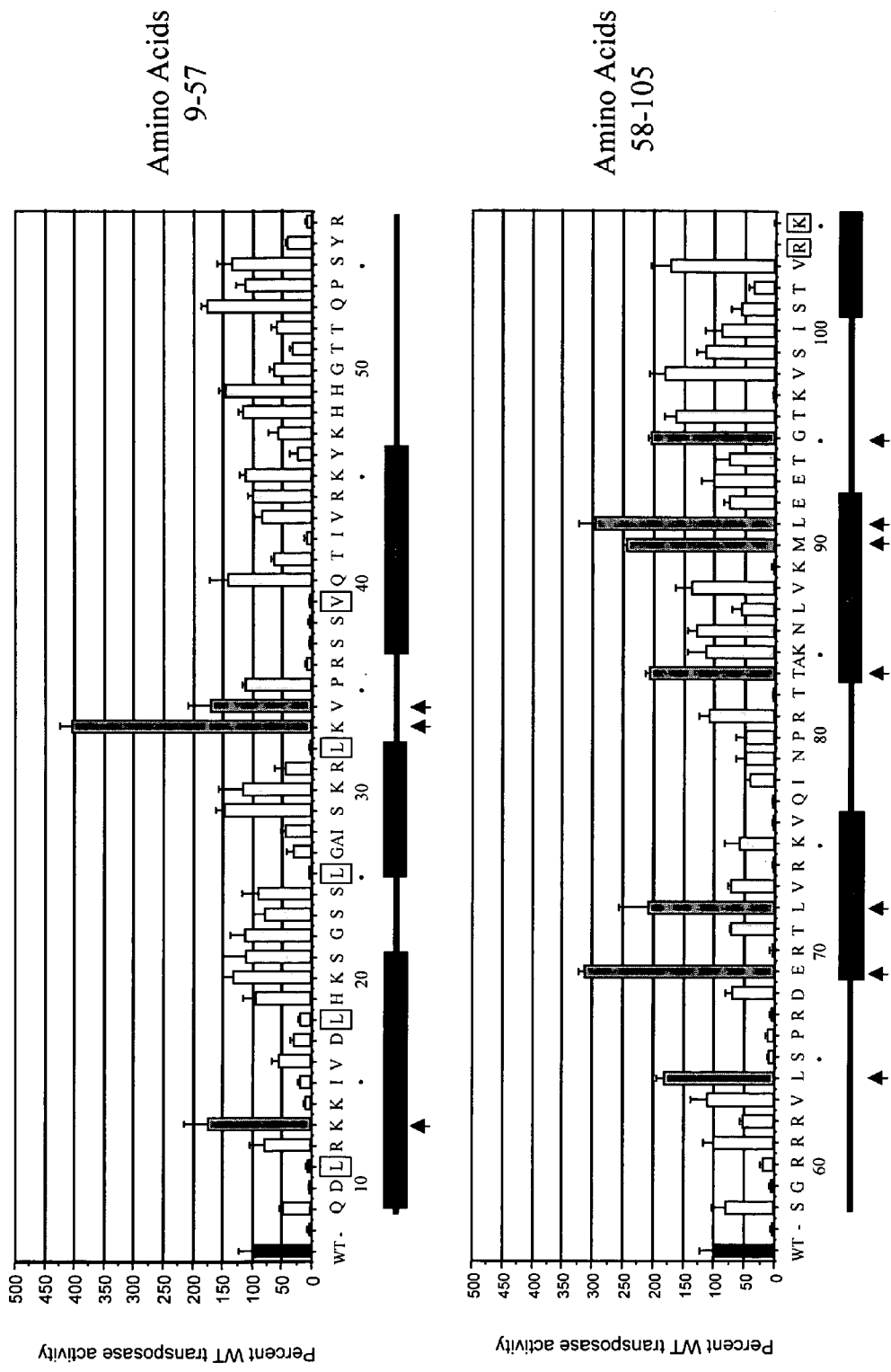
FIG. 3. shows transposition activity of mutated SB transposases in HeLa cells. HeLa cells were co-transfected with a plasmid encoding a neomycin-marked transposon (pT-nori) together with a plasmid encoding either the original SB wild-type (WT) or transposase mutants containing alanine residues at various positions in the transposase N-terminus. Two days later, transfected cells were diluted into medium containing G418 (600 µg/ml), growth selected for two weeks, and the $G418^R$ colonies fixed, stained and counted. The average colony counts±st.dev obtained after three independent experiments is shown. The transposition activity for each transposase mutant is shown relative to the wild-type transposase, which was adjusted to 100%. The sequence of residues 9-105 (SEQ ID NO:26) of the wild-type transposase are provided below the graphs. The location of the helical DNA-binding domains is shown, as well as the residues which comprise the leucine zipper and nuclear localization domains (boxed).

Results of these studies are shown in FIG. 3 and indicate that hyperactivity can result from alanine substitution at numerous positions in the SB transposase. Thirty-two of these mutations (D10A, L11A, K14A, I15A, D17A, L18A, L25A, G26A, L32A, R36A, S37A, S38A, V39A, I42A, Y46A, T51A, R57A, G59A, R60A, S65A, P66A, R67A, R70A, R74A, V76A, Q77A, Y82A, K89A, K97A, T102A, K104A, and R105A) reduced transposition frequency to barely detectable levels. In addition, two mutations (T41A and G50A) reduced transposition to 65% of WT, and each of fourteen additional mutations reduced activity to 42-59% of WT. We also identified ten amino-acid-substitutions that resulted in significant levels of hyperactivity. Compared to the WT, mutation K33A improved SB's transpositional activity 400%, whereas each of the E69A and L91A mutations improved its activity 300%. In addition, one mutation, M90A, increased SB's transposition activity 2.5-fold, whereas six independent mutations improved its activity 2-fold (L72A, T83A, and G95A) and ~1.7-fold (K13A, L64A, and V34A). Overall, these studies identify a number of residues important for transposase function and demonstrate proof-of-principle that molecular evolution can be used to significantly improve transposase performance in mammalian cells.

B. DNA Binding Activity for Single Amino Acid SB Mutants.

Since approximately half of the N-terminal missense mutations we analyzed showed a reduced ability to mediate transposition in mammalian cells, we tested whether these mutant proteins could still interact efficiently with transposon end sequences, a necessary first-step in the transposition process. To do this, we produced N123 fragments corresponding to the DNA-recognition domains of wild-type (WT) and mutant SB transposases and then measured the ability of each peptide to interact with double-stranded oligonucleotides corresponding to SB's binding sites using an electrophoretic mobility shift assay (EMSA).

Figure 4:
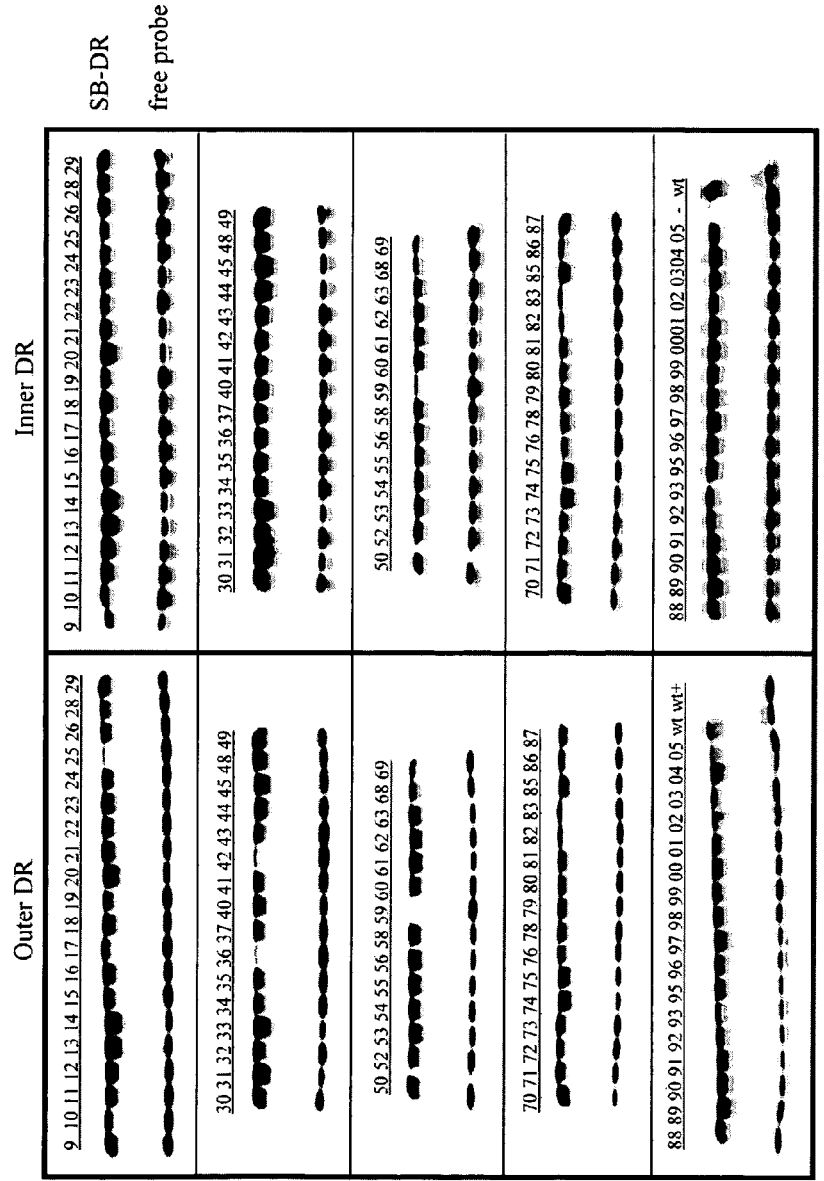
FIG. 4. shows the effects of single-amino-acid transposase mutations on transposon DNA binding activities. The N123 peptides from WT and mutant transposases were complexed with double-stranded radiolabeled oligos encoding the outer DR (SEQ ID NO:18) (bottom panel, left column) or inner DR (SEQ ID NO:19)(bottom panel, right column) sequences. Numbers represent the amino acid residue in SB that was mutated to alanine. Shown also is an alignment of SB's DR sequences (top panel), with identical nucleotides shaded in gray. DR, direct repeat; –, no transposase control; wt+, WT SB-DNA complexes were formed in the presence of 500-fold unlabeled oligonucleotide as a specific competitor.

Results of these analyses showed that the vast majority of these alanine-substitution mutants retained significant levels of binding activity with respect to both the inner and outer transposon direct repeats (FIG. 4, bottom panel). The results show that the major defect in the majority of the transpositionally-inactive SB mutants described herein occurs at a step subsequent to transposon end binding, with a few notable exceptions. For instance, the three nonfunctional mutants L25A, R36A and I42A were each capable of binding the inner DR sequences but were significantly diminished in their ability to mediate binding to the outer DRs (FIG. 4, bottom panel, rows 1 and 2). In addition, the inactive G59A mutant showed a more general defect in the ability to mediate transposon end binding (FIG. 4, bottom panel row 3). These results show that leucine 25, arginine 36 and isoleucine 42 each play a critical role in mediating critical DNA contacts specifically with the ends of the transposon. Moreover, they show that glycine 59 is involved in mediating critical contacts with conserved portions of the inner and outer DR sequences, although an essential role for this residue in ensuring the proper folding of the transposase N-terminus cannot be ruled out. The study showed that the mutant proteins are still capable of efficiently interacting with the end sequences of the transposon, which such interaction is a necessary step in the transposition process.

C. Combinations of Hyperactive Mutations can Further Improve Transposition Efficiencies.

Figure 5:
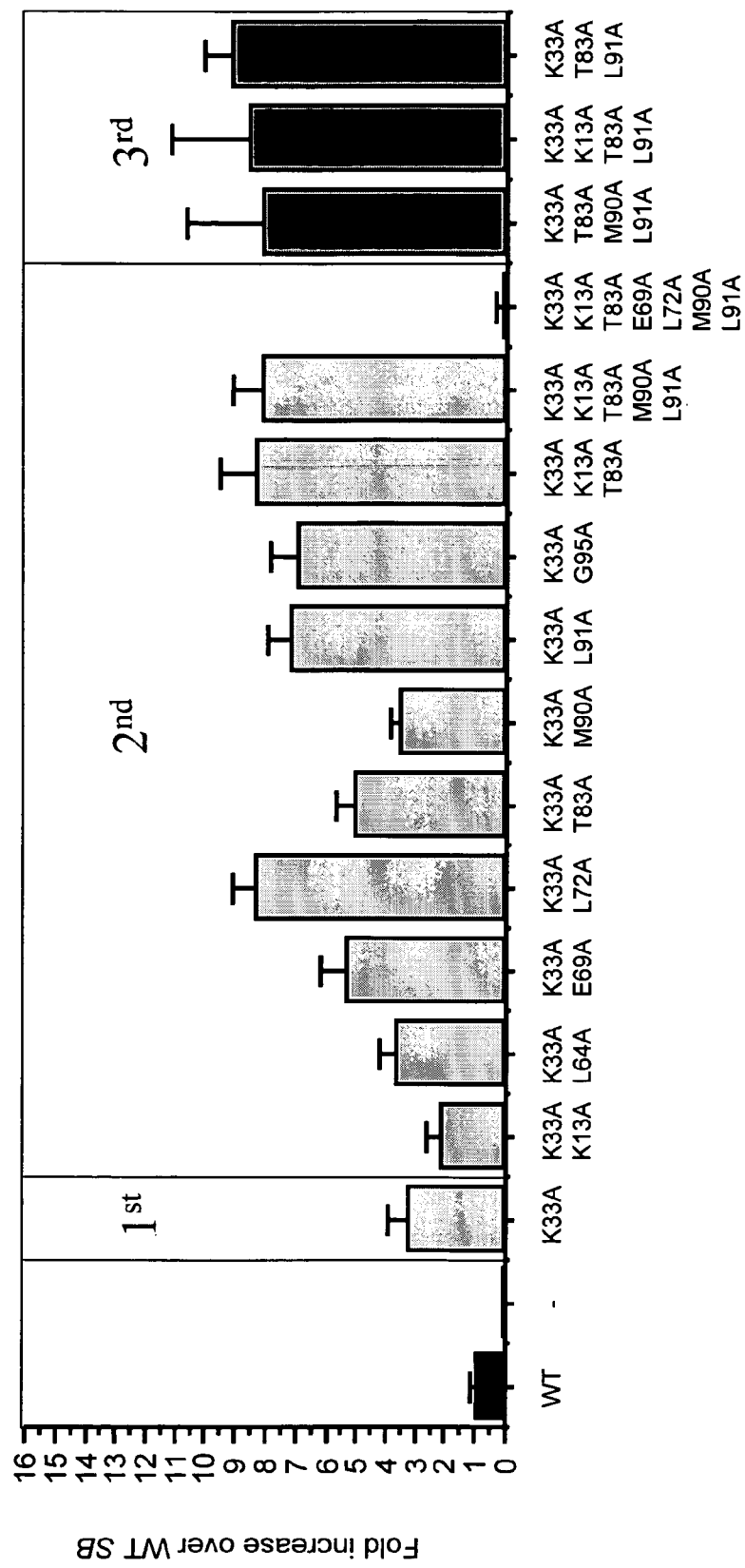
FIG. 5. shows transposition activity of SB transposase mutants containing multiple hyperactive mutations. Each hyperactive mutation was combined first with the best single hyperactive mutant (SB-K33A) alone, and then with various additional hyperactive mutations. Each of these mutants was tested for improved transposition of a neomycin transposon (pT-nori) in HeLa cells and then further optimized by systematically removing combinations which adversely affected the transposition efficiency. HSB, hyperactive SB mutant.

We individually combined each of eight hyperactive mutations with the K33A mutation and then sequentially combined positive hyperactive combinations and removed any dampening mutations in the K33A background. Results of these studies are shown in FIG. 5 and demonstrate that while certain combinations of hyperactive mutations could facilitate transposase performance by more than 9-fold relative to the wild-type transposase, other combinations completely inactivated transposase's integration activity in cells. In the end, we were able to generate a series of transposase variants with markedly improved integration capabilities, including four hypersensitive SB mutants (HSB1 through 4) that could support as much as 9-fold improved transposition frequencies as compared to WT protein.

D. Combined Use of an Improved Transposon (pT3) and Hyperactive Transposases Increases the Frequency of Transgene Integration in Mammalian Cells.

Figure 6B:
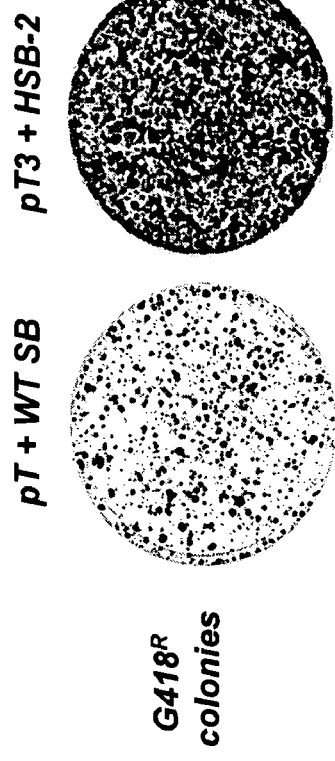
Figure 6C:
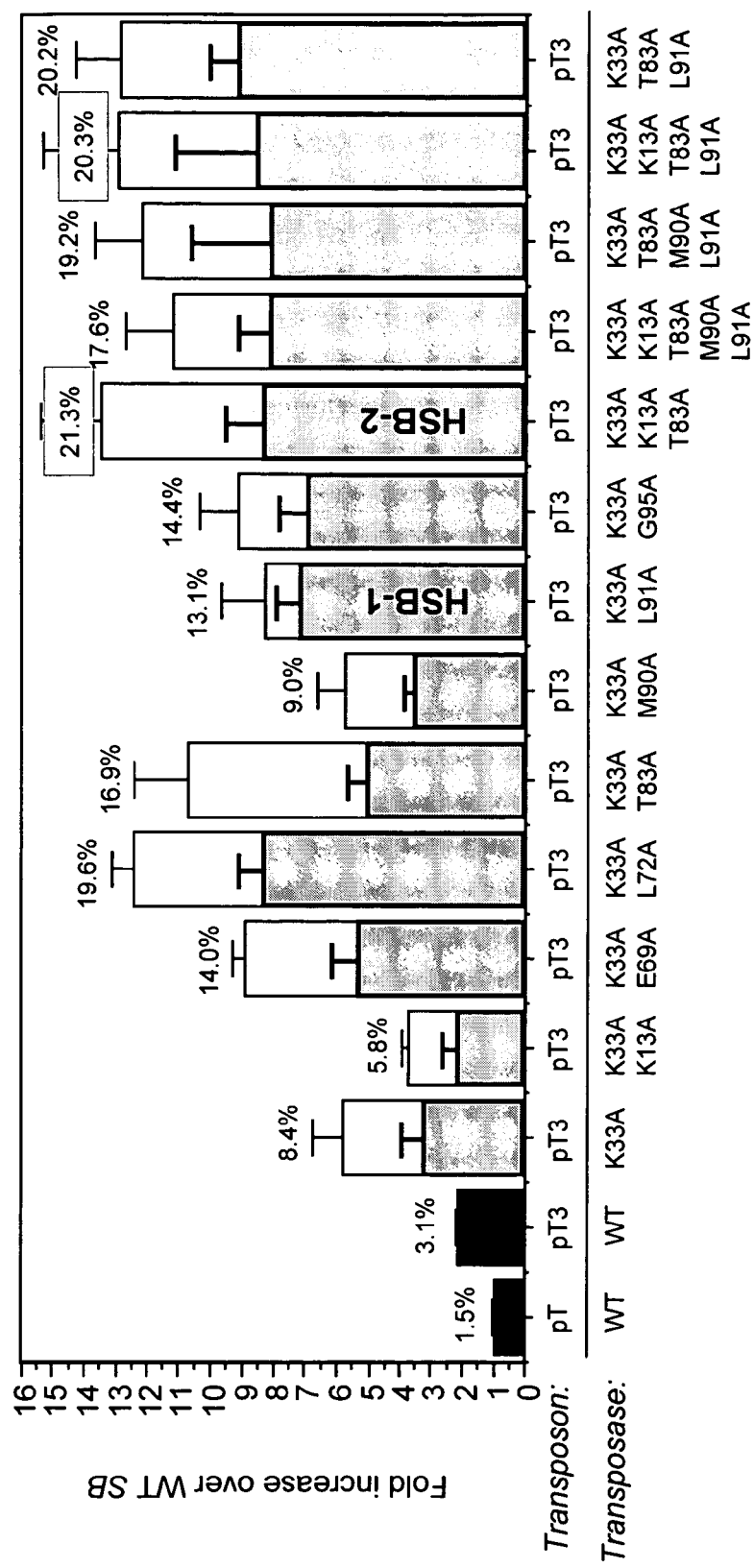

We studied whether transposition frequencies could be further increased by combining the use of hyperactive transposases with a new transposon vector, pT3. This vector contains an extra transposition enhancer sequence and an additional TA dinucleotide, both of which should promote transposon excision (FIG. 6A). Results are shown in FIG. 6B, C and demonstrate additional improvements in the integration frequencies in cells. Indeed, the use of pT3 together with one hyperactive SB mutant, HSB-3, resulted in a >13-fold improvement in DNA transposition frequencies in mammalian cells relative to the wild-type SB transposase/transposon system.

Figure 7:
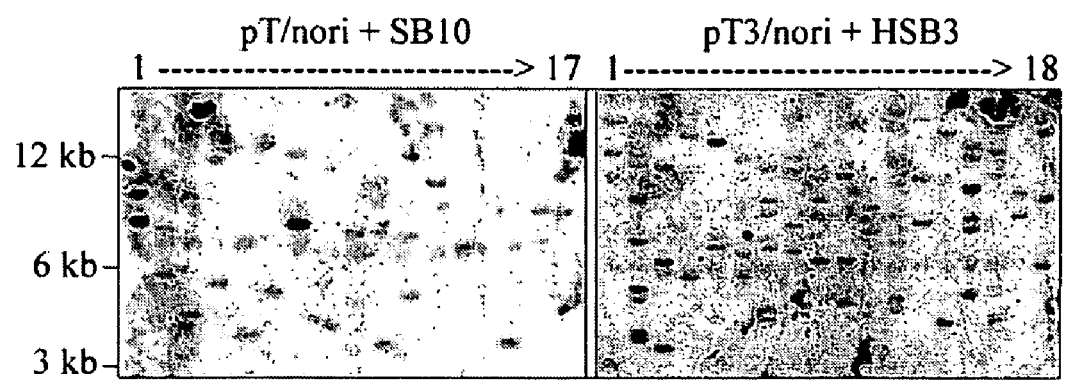
FIG. 7. is a southern blot of transposon copy number analysis in HeLa cells stably transfected with the WT and hyperactive SB systems. Each DNA sample, isolated from expanded G418 resistant HeLa colonies, was digested with BamHI (cuts once in the transposon) and analyzed by Southern blot analysis using a neo probe.

We studied the average number of transposon insertions per HeLa cell genome following stable transfection with either WT or hyperactive SB systems. By Southern blot analysis, the WT system was found to produce an average of 1-2 transposon insertions per genome (FIG. 7, left panel), whereas this value was increased approximately threefold with the hyperactive system, with two $G418_R$ clones each showing ten independent insertions (FIG. 7, right panel, see lanes 2 and 12).

D. DNA-binding Affinities of the Hyperactive SB Mutants.

Figure 8:
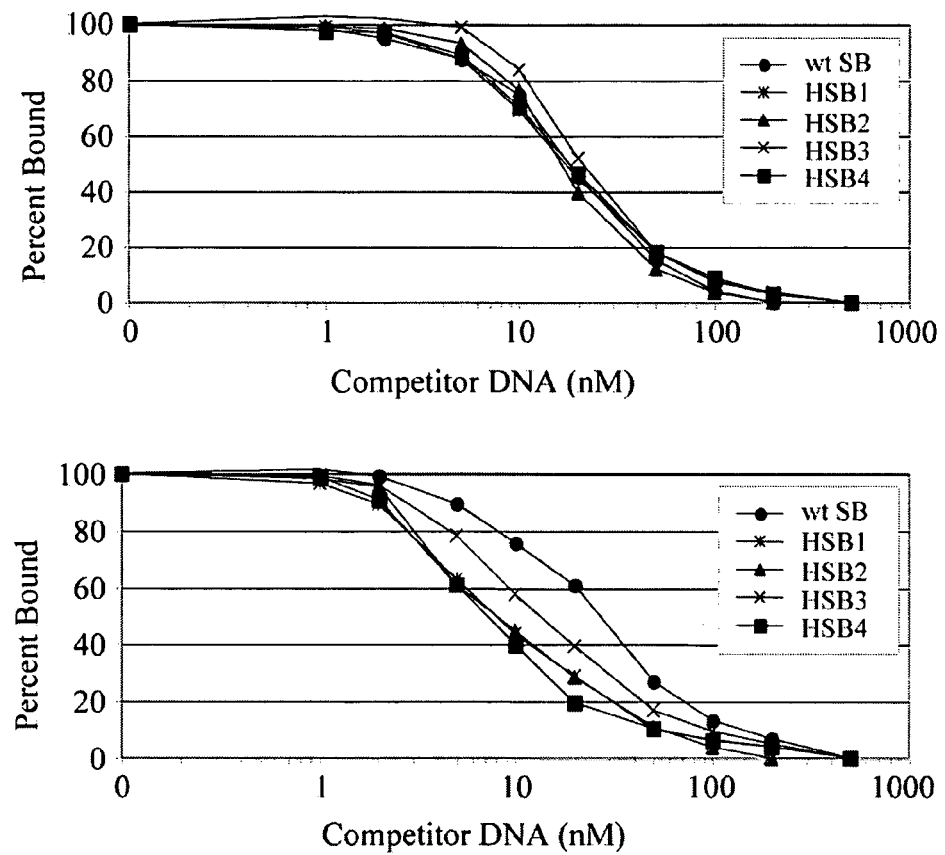
FIG. 8. is a comparison of the relative binding affinities of the WT and HSB mutants for transposon binding sites. SB-N123 peptides for WT and hyperactive transposases were complexed with double-stranded radiolabeled oligos encoding the inner (top panel) or outer (bottom panel) DR sequences. Protein-DNA complexes were formed in the presence of increasing amounts of the corresponding unlabeled oligonucleotide. The percent binding was determined using a Phosphorimager and normalized according to the amount of probe bound in the absence of any competitor minus the amount of probe bound at 500 nM.

Previous work with the bacterial element Tn5 has indicated that transposase hyperactivity may originate from an enhanced affinity of the transposase for the transposon IRs (Zhou et al., 1997, J. Mol. Bio., 271:362-373). Therefore, we measured the affinity of WT and mutant SB proteins for the ends of the element by EMSA. Results of these analyses revealed that there was no change in the binding affinity of any of the proteins for the inner DRs (FIG. 8, top panel). Interestingly, each of the four HSB (hyperactive SB) mutants showed significantly stronger binding to the outer DR sequences compared to WT, with HSB1, HSB2, and HSB4 all showing a 3- to 4-fold greater affinity for these outer DR sequences, and a 2-fold higher affinity for HSB3 (FIG. 8, bottom panel). Accordingly, mutations that alter SB's DNA-binding capabilities also enhance its transpositional activity in mammalian cells. Moreover, the results showed that the hyperactivity of the four HSB mutants originates from an enhanced affinity of the mutant transposases to the outer DR sequences of the transposon.

E. Donor DNA Cleavage Activity.

Figure 9:
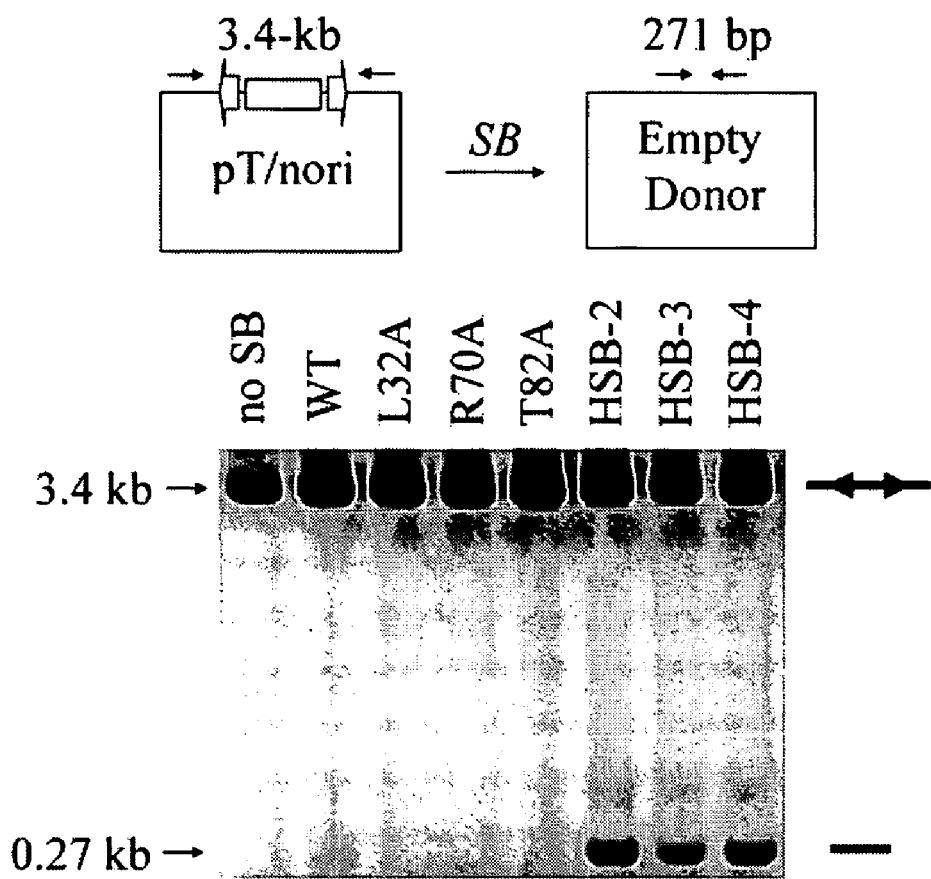
FIG. 9. shows the effects of amino acid substitutions on donor DNA cleavage activity in human cells. A transposon donor plasmid was transiently transfected into HeLa cells either alone or in combination with a transposase plasmid, and the DNA isolated 30 h later for PCR analyses with primers flanking the donor element. Donor plasmids that have undergone SB-mediated transposon excision and double-strand break support the amplification of a 271-bp product. The amount of SB element excision produced in the presence of inactive (lanes 3-5) and hyperactive (lanes 6-8) SB mutants is shown relative to WT.

To study the cleavage activity of the mutant proteins, we isolated plasmid DNA from HeLa cells transiently transfected with transposon donor and transposase-expressing constructs and subjected these DNAs to PCR using primers flanking the donor element. In contrast to control cells expressing either no transposase or three transpositionally inactive SB mutants (FIG. 9, lanes 1 and 3-5, respectively), cells expressing the WT transposase supported the production of a 271 bp product of excision and double-strand break repair (FIG. 9, lane 2). This product was cloned and sequenced, and was found to contain a TA-flanked 3-bp footprint at the excision site, which is consistent with SB-mediated DNA cleavage activity (Yant et al., 2003). Interestingly, when we compared the relative amount of excision and double-strand break repair product made under each experimental condition, we found that the HSB mutants all displayed substantially elevated donor DNA cleavage activity in HeLa cells relative to WT (FIG. 9, lanes 2 and 6-8). We estimated the amount of these products by limiting dilution PCR and found ~3- to 4-fold higher cleavage activity for the HSB mutants compared to WT. Therefore, the results further demonstrate that improved binding to the ends of the transposon significantly enhances more downstream events in the transpositional reaction, including the rate at which a target SB element is excised in vertebrate cells.

F. Chromosomal Transposition.

Figure 10:
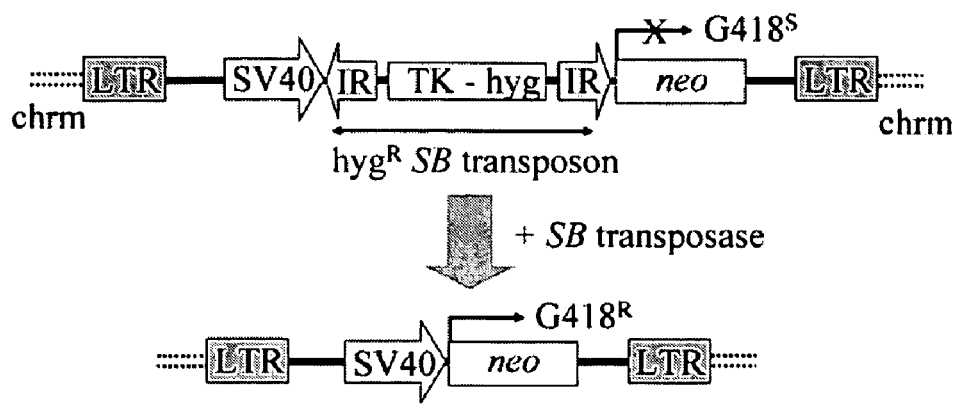
FIG. 10. shows the effect of transposase hyperactivity on chromosomal transposition rates. The top panel is a schematic representation of the genetic assay for detecting rare chromosomal transposition events. A neomycin resistance (neo) gene under the control of simian virus 40 (SV40) promoter is inactivated by the insertion of a nonautonomous SB element containing a hygromycin resistance (hygR) gene driven by the thymidine kinase (TK) promoter. This construct is packaged into a lentivirus and randomly integrated as a single-copy provirus into the genomes of infected HeLa cells. Transient expression of active SB transposase in these cells results in excision of the SB element and activated expression of the neo gene, resulting in G418 drug-resistant growth. LTR, HIV-1 long terminal repeat. The bottom panel shows transposition frequencies in HeLa cells using WT and hyperactive transposase. Three different reporter cell lines were each transiently transfected with plasmids encoding GFP as a control, WT SB, or HSB3. Cells were growth-selected in G418 for 3 weeks and resulting colonies were fixed, stained and counted. ND, none detected.

In contrast to the efficient SB transposition from extrachromosomal plasmids, the frequency at which chromosomally located SB elements are mobilized in mouse embryonic stem cells and human HeLa cells is exceptionally low ($\sim 10^{-6}$ events per transfected cell) (Luo et al., 1998, PNAS 95:10769-10773; Yant et al., 2003). We therefore tested whether transposase hyperactivity could improve SB mobility from mammalian cell chromosomes. To do this, we used a stably-integrated excision reporter construct to permit G418 selection of SB element chromosomal excision events following transient transposase expression (FIG. 10, top panel). We generated three reporter lines, each containing a single copy of the excision reporter construct integrated at different genomic loci, and selected for G418-resistant growth following transfection with plasmids encoding green fluorescent protein (GFP) as a control, WT SB, or HSB3. Although the WT enzyme induced chromosomal transposition at the expected frequency, the HSB3 mutant increased this frequency by 4- to 5-fold in each of the three reporter cell lines (FIG. 10, bottom panel). Accordingly, the results show that the hyperactive transposase mutants are capable of facilitating an increased mobilization of transposable elements from mammalian cell chromosomes in vitro.

G. Hyperactive Transposase Mutants Support Improved Integration Efficiencies in Vivo.

Figure 11A:
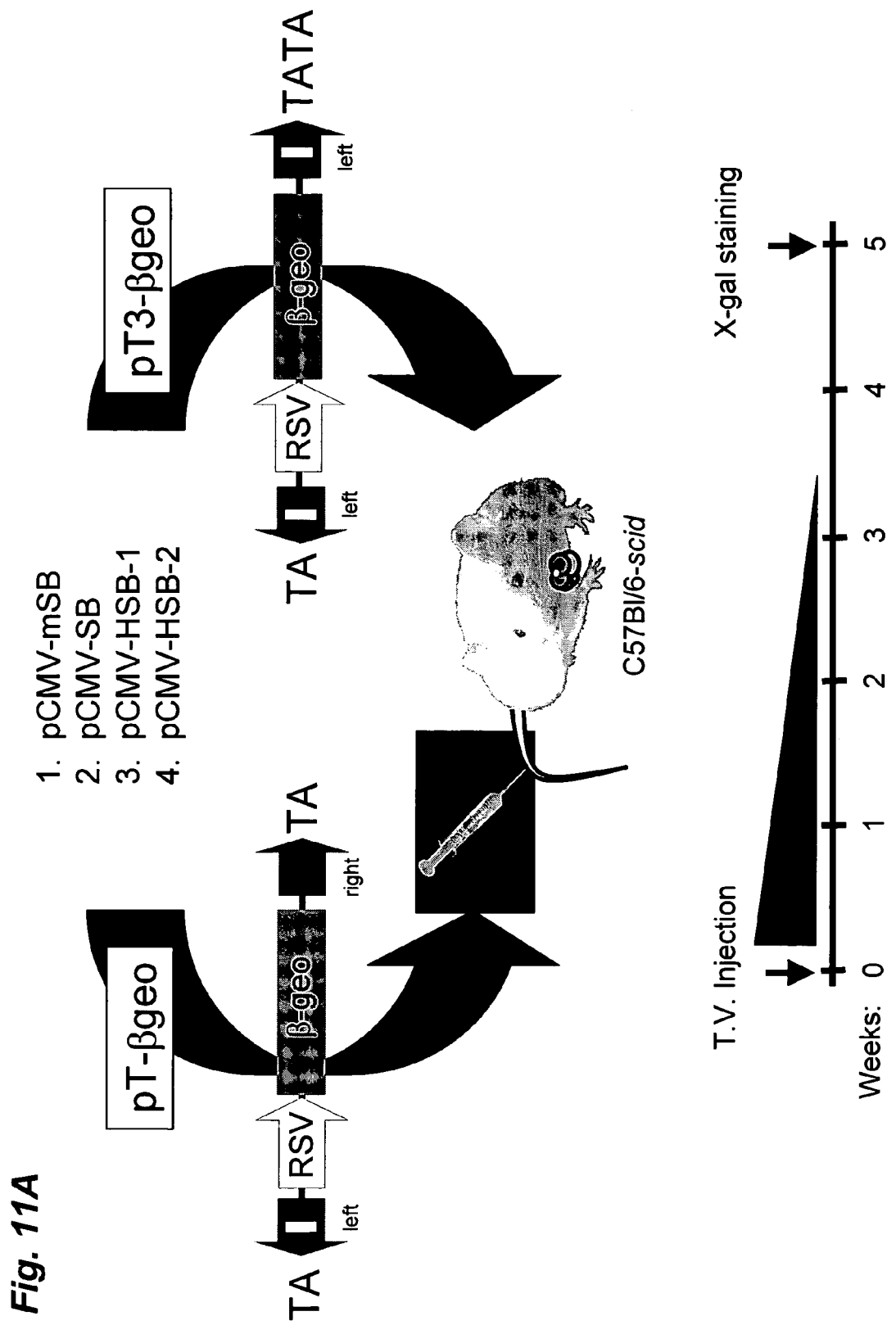
FIGS. 11A-B. show β-galactosidase expression in mouse liver following administration of improved transposase/transposon vectors.
Figure 11B:
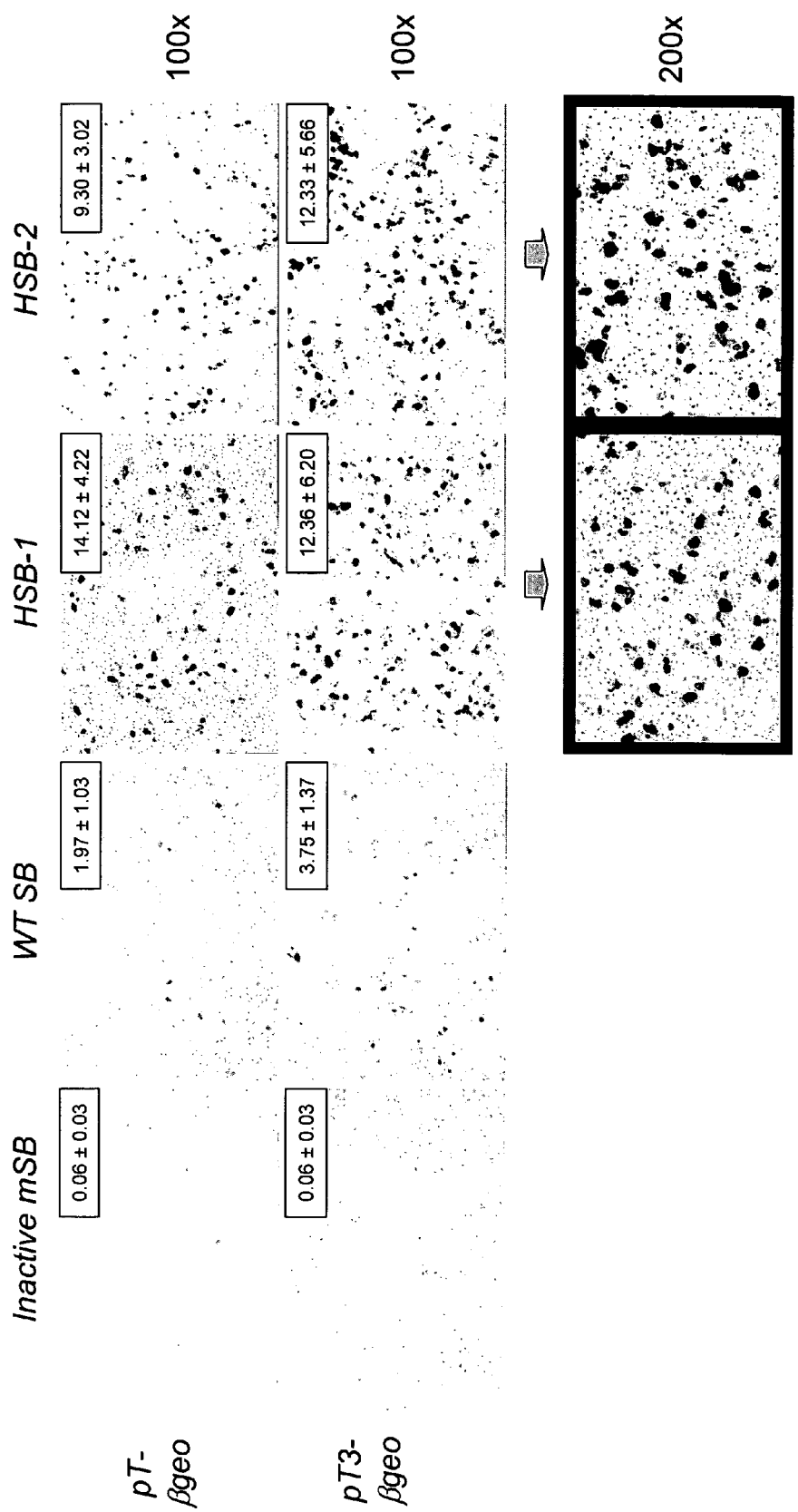

A hyperactive DNA transposition system would greatly facilitate persistent gene transfer in mammals, and might improve gene discovery in vertebrates. We therefore tested whether the improvements observed in culture were also active in vivo. To do this, we administered plasmids encoding a β-galactosidase-marked transposon together with a transposase plasmid to the livers of mice via a rapid tail vein injection (FIG. 11A). We then monitored the persistence of reporter gene expression 5 weeks after vector administration by X-gal staining in order to quantify the number of hepatocytes which had undergone transposition events. Results are shown in FIG. 11B and demonstrate as much as a 7-fold improvement in the transposition frequencies in vivo using either hyperactive transposase alone or together with an improved transposon vector.

H. The Efficiency of Sleeping Beauty (SB) Element Transposition in Human Cells is Variably Affected by Single-amino-acid Substitutions within the Transposase's Catalytic Core Domain.

Based on its direct role in catalysis, we hypothesized that altering the amino acid sequence in the regions surrounding the catalytic triad should have profound effects on the protein's enzymatic activity. We therefore introduced alanine-substitution mutations into the 3' end of the SB transposase gene by PCR and screened mutant enzymes for altered activity in human cells using a genetic transposition assay. This screen involved co-transfecting HeLa cells with a donor plasmid encoding a neomycin-marked SB transposon (pT/nori) together with a plasmid expressing either the mutated transposases or the wild-type SB protein as a reference control. Cells were then placed under antibiotic (G418) selection and the numbers of G418-resistant ($G418^R$) colonies compared to wild-type as a measure of the relative transpositional efficiency.

We analyzed a total of forty-six different single-amino-acid substitution mutants for SB and found widely variable effects of these mutations on transposase integration activity (FIG. 12A). Twenty-six of these mutations (W239A, F241A, Q241A, D244A, N245A, D246A, P247A, K248A, H249A, W257A, L258A, V263A, L266A, W268A, P269A, Q271A, S272A, P273A, D274A, N276A, I278A, E279A, N280A, L281A, W282A, and L285A) reduced transposition frequency to barely detectable levels, whereas K256A and E284A reduced transposition to about 60% and 50%, respectively. These functional differences were not due to changes in protein expression and/or stability since western blot analyses indicated similar steady-state levels for each mutant relative to wild-type (FIG. 12B). Collectively, these results suggest the presence of at least three major subdomains within the catalytic core that are important for SB transpositional activity. These include domains I (residues 239-249) and II (residues 268-285), which encompass the conserved catalytic aspartate (D244) and glutamate (E279) residues and appear to play dominant roles in transposition activity, as well as a less tightly constrained linker region (domain III, amino acids 250-267) in which single-amino-acid substitutions are tolerated much better in comparison to either domain I or II.

In the course of this screen, we also identified six alanine-substitution mutations (M243A, K252A, V254A, D260A, S270A, and P277A) that significantly improved transpositional activity in human cells. These mutations were distributed among each of the identified subdomains, with mutations S270A and V254A showing the highest overall integration activity, corresponding respectively to 186 and 142% of wild-type. Interestingly, the hyperactive mutation M243A is located immediately adjacent to the highly conserved D244 residue and is the only amino acid within domain I that is not negatively affected by alanine substitution. A similar general trend was also observed for hyperactive mutations S270A and P277A, each of which resides near the conserved E279 catalytic residue located within in the tightly constrained domain II.

In conclusion, the results from these studies show that single-amino-acid mutations within the C-terminal catalytic core region of SB can also profoundly affect transposase function in mammalian cells.

I. The S270A Mutation Acts Synergistically with Three N-terminal Hyperactive Mutations (K13A/K33A/T83A).

Figure 13:
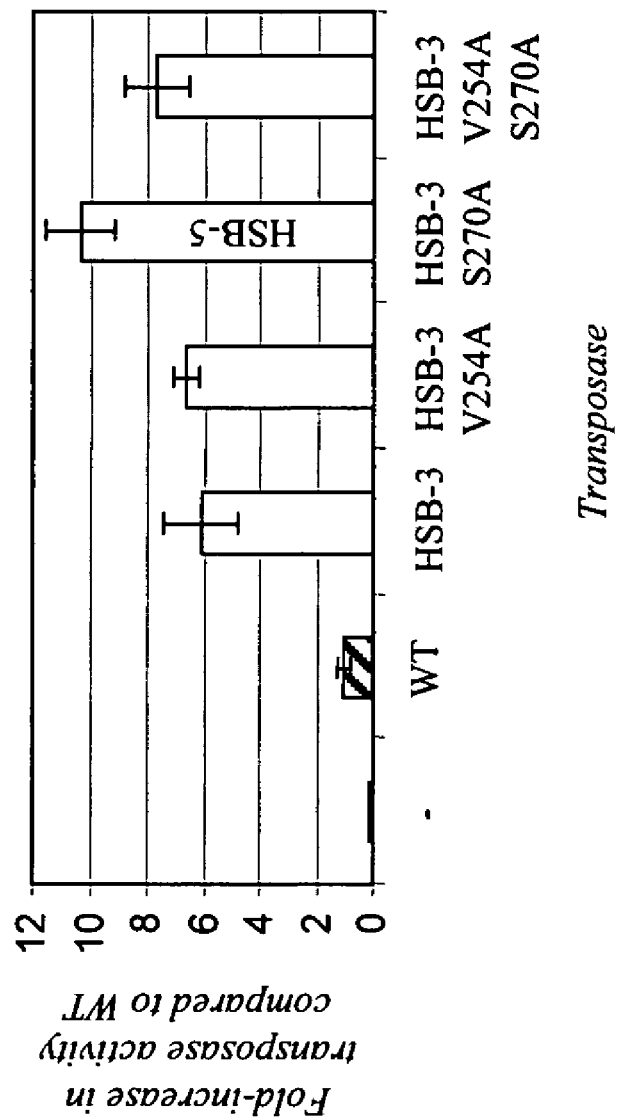
FIG. 13. shows the effects of N-terminal and C-terminal hyperactive mutations in combinations. Transposition was assayed in human HeLa cells, and the activity of wild-type transposase (stripped column) is taken as a reference and adjusted to 100%.

Our preliminary screen of the SB catalytic core identified many single-amino-acid mutations that resulted in significant transposase hyperactivity. Here we tested whether combinations of these hyperactive mutations resulted in an additive or synergistic effect. For these purposes, we engineered our two best hyperactive C-terminal mutations (V254A and S270A), either individually or together, into hyperactive SB-3 (HSB-3) transposase mutant containing three amino-acid-substitutions (K13A, K33A and T83A) within the bipartite, DNA-binding domain of the transposase N-terminus. Although the transposition efficiency of the quadruple mutant K13A/K33A/T83A/V254A was not markedly improved compared to HSB-3, the combined addition of V254A and S270A mutations to HSB-3 increased its transposition activity by 1.6-fold (FIG. 13). Moreover, the singular addition of mutation S270A improved HSB-3 activity 4.2-fold, suggesting that S270A acts synergistically with K13A/K33A/T83A. This quadruple K13A/K33A/T83A/S270A mutant transposase (hereafter referred to as HSB-5) elevates SB element transposition in mammalian cells by more than 10-fold compared to the wild-type protein, making it the most active SB version described to date. As such, these results show that a site-directed mutagenesis approach is a viable and powerful method for generating tranposases with increased transposition capabilities. Moreover, the results show that a mutant transposase that has mutations in the N-terminal and C-terminal portions of the protein possesses elevated SB element transposition in mammalian cells as compared to the wild-type protein.

J. Wild-type and Hyperactive Transposases are Still Regulated by Multi-copy Inhibition.

Figure 14:
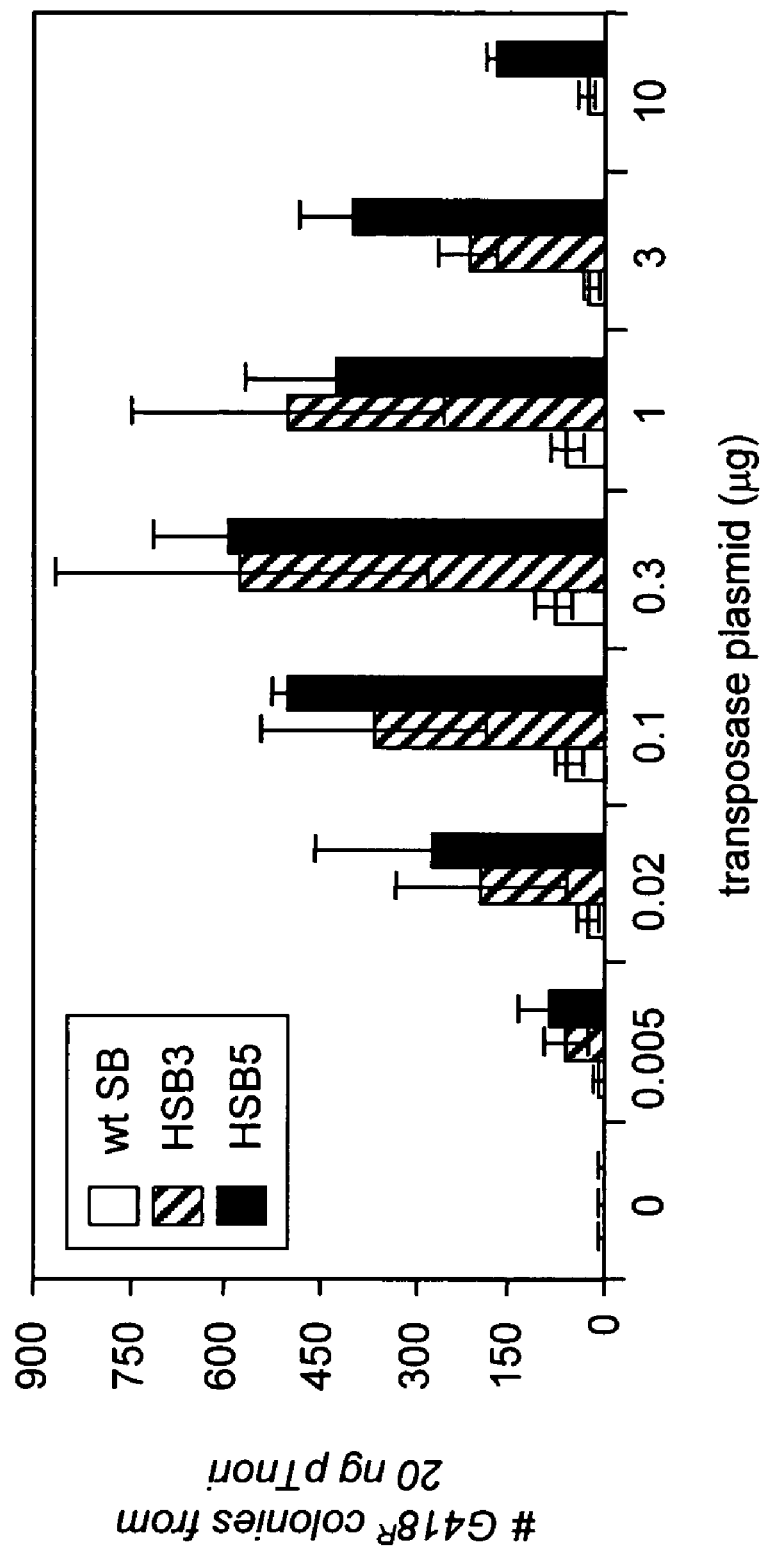
FIG. 14. shows the effects of increased transposase expression on the frequency of transposition in cultured mammalian cells. HeLa cells were transfected with 20 ng pT/nori together with increasing amounts of helper plasmids encoding either wild-type SB (white columns) or the K33A/T83A/L91A hyperactive mutant transposase HSB-4 (black columns). In all transfections, the appropriate amount of empty vector (pc-N) was added as filler to maintain a constant amount of DNA per transfection. The mean number of G418$^R$ colonies±standard deviations obtained 14 days after three independent transfections is shown.

Cellular concentration of transposase can be a limiting factor of transposition under certain conditions. For example, the expression of transposase beyond a certain threshold level has a significant negative impact on transposition. This phenomenom is termed overproduction inhibition and has been observed both in cultured cells and in vivo in mouse liver. Here we tested whether the increased activities of either HSB-3 or HSB-5 could be due, at least in part, to a reduced sensitivity of these enzymes to overproduction inhibition. To do this, we transfected HeLa cells with a constant amount (20 ng) of pT/nori together with increasing amounts of plasmids encoding wild-type or hyperactive transposase mutants, and then tested what effect increased transposase expression had on the transposition efficiency. To maintain a constant amount of DNA in each transfection, we also included an empty plasmid (pc-null) as a stuffer. Irrespective of the ratio of transposon to transposase plasmid DNA, the results showed a significant improvement in the transposition frequency in the presence of the hyperactive mutants as compared with the wild-type transposase (FIG. 14). However, the transposition efficiency obtained with both mutants still dropped at high transposase-to-transposon ratios, indicating that the mechanism of hyperactivity is not related to the elimination of multi-copy inhibitory pathways. Accordingly, the results show that the increased activities of HSB-3 and HSB-5 are not a result of a reduced sensitivity of the enzymes to overproduction inhibition. Moreover, the data indicates that a much smaller dose of hyperactive transposase will be required for efficient gene delivery, which could be used to dramatically improve its safety profile in vivo.

K. Hyperactive Transposases can Significantly Improve the Transposition Efficiency for Large SB Elements.

Figure 15A:
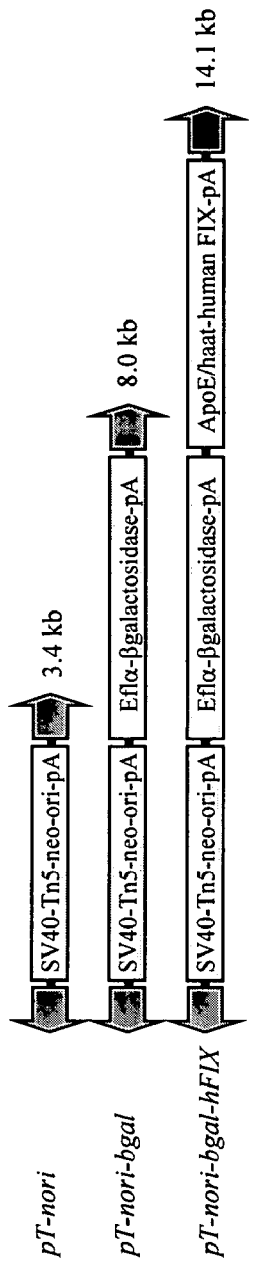
FIG. 15A-C. show an analysis of transposase activity relative to transposon size.
Figure 15C:
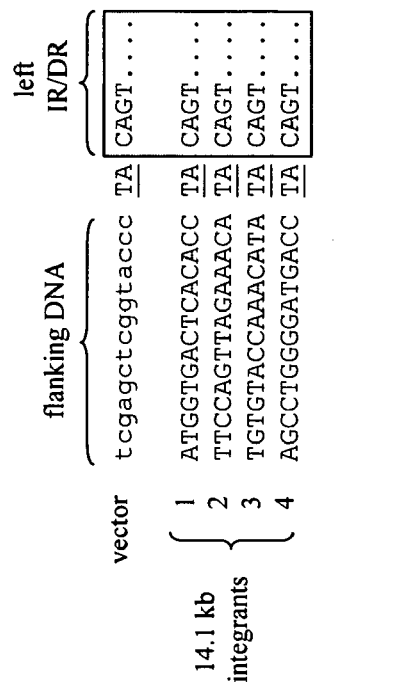
Figure 15B:
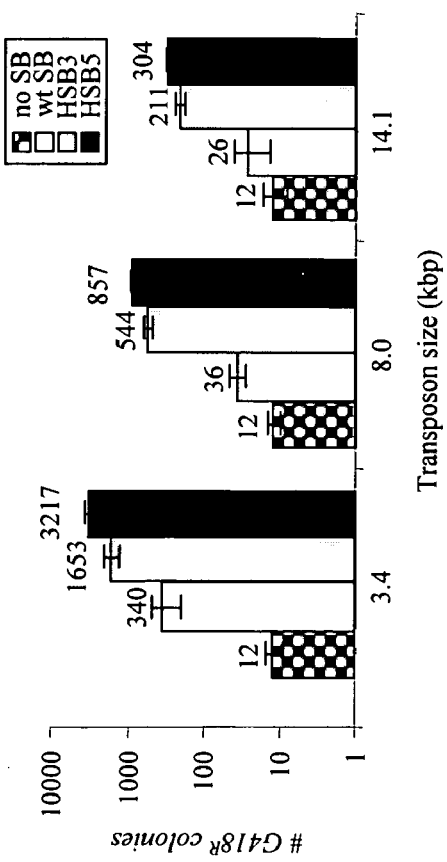

One limitation of the SB system is that transposition rates with SB are inversely proportional to the length of the transposon. One possible way to improve transposition of large-size elements is to improve the stability of the transposase/transposon complex, potentially through the use of hyperactive transposase mutants. Here we tested what effect transposase hyperactivity had on the integration frequency of larger-sized SB elements. We first engineered donor plasmids containing 3.4, 8.0, or 14.1 kb long neomycin-marked elements by introducing various lengths of stuffer DNA. We then tested the transposition efficiency for these constructs in the presence of the wild-type or hyperactive transposases using the in vivo transposition assay. Results obtained with the wild-type transposase are consistent with previous reports and showed a reduction in the transposition efficiency for the 8.0 kb transposon, and an even more dramatic decline for the 14.1 kb element, relative to the 3.4 kb element. Although we still observed a significant drop in the transposition frequency in the presence of hyperactive transposase mutants, the HSB-3 and HSB-5 mutants were respectively 8-fold and 12-fold better at integrating transposons as large as 14.1 kb compared to the wild-type (FIG. 15B). Furthermore, we could verify that integration of the 14.1 kb element was indeed due to SB-mediated transposition because we recovered integrated elements from the genome of four randomly selected G418$^R$ HeLa clones using a plasmid recovery strategy. Analysis of the junction sequences for these elements showed flanking TA dinucleotides, followed by sequences that differed from those originally flanking the transposon in the parental plasmid (FIG. 15C). These results are consistent with transposition rather than random (illegitimate) recombination-based processes and remain the largest transposed SB elements shown to date.

Accordingly, the data shows that the hyperactive SB transposase mutants can significantly enhance the transposition of large-size transposable elements, thereby providing a valuable new approach to improve the stable delivery of large transgenes for human gene therapy applications.

L. The K13A/K33A/T83A Triple SB Mutant Facilitates Improved Gene Transfer Efficiencies in Mice.

Figure 16:
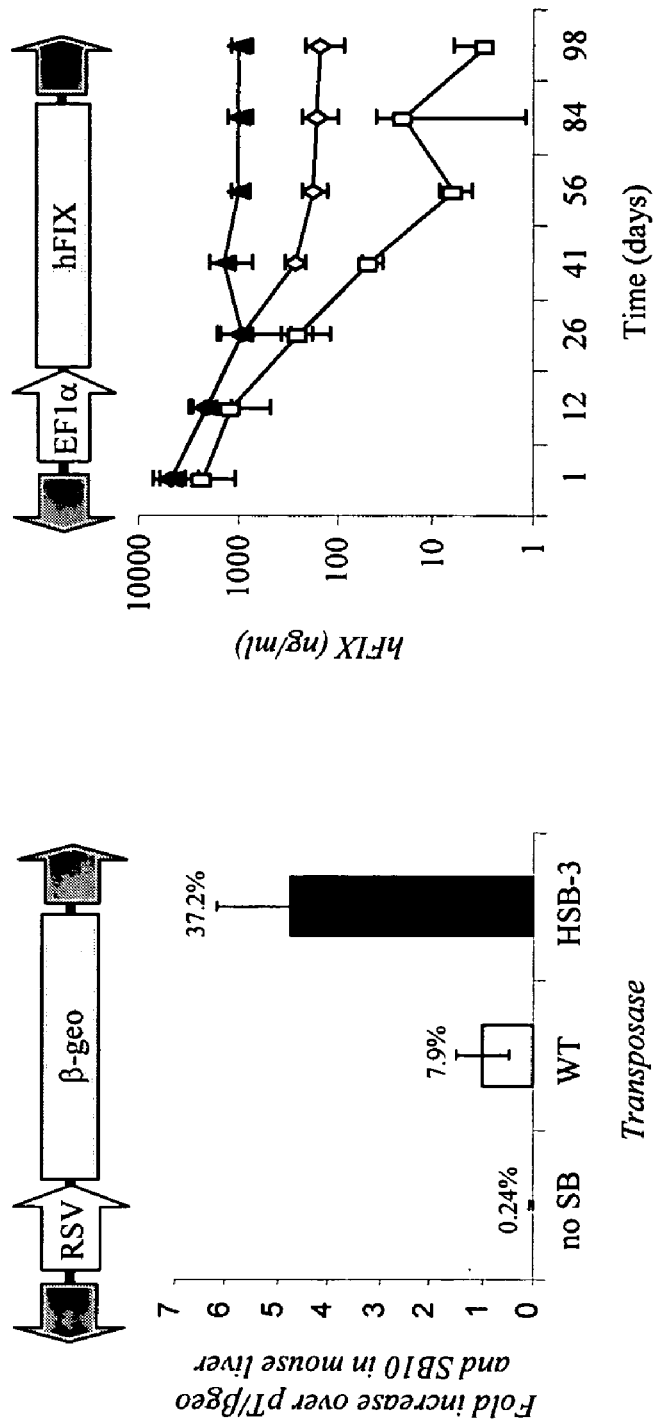
FIG. 16. shows a comparison of gene transfer activity of wild-type and hyperactive transposases in mouse liver. The left panle shows the transposition efficiency in mouse liver using wild-type and mutant transposases. C57Bl/6-scid mice (n=4-5 mice per group) were injected via the tail vein with 25 μg pT/βgeo together with 1 μg of plasmids encoding no transposase, wild-type SB, or the hyperactive mutant transposase HSB3. Mice were sacrificed five weeks later and their livers sectioned and stained for β-galactosidase expression to determine the mean number of X-gal-positive hepatocytes±st.dev observed under each experimental condition. The transposition efficiency for wild-type transposase plus pT/βgeo was adjusted to 100% and other combinations are shown as relative activities. Noted above each bar are the percentage of mouse hepatocytes that received pT/βgeo (estimated to be ~25% of total, as determined 2 days post-injection in control mice) and remained X-gal positive five weeks post-injection. The right panel shows serum human factor IX (hFIX) concentrations in mice following transposon DNA injection. C57Bl/6 mice (n=5 mice per group) were injected via the tail vein with 25 μg pT/hFIX together with 1 μg of plasmids encoding HSB-3 (triangles), wild-type SB (diamonds) or no transposase (squares) as a control. Mean values±standard deviations are shown.

In order to demonstrate that the hyperactive transposase mutants function in vivo we produced a SB transposon encoding β-galactosidase (FIG. 16, left panel) and delivered this vector in vivo to immune-deficient C57Bl/6-scid mice via a rapid tail vein injection. This hydrodynamic-based delivery method results in efficient but transient transfection of mouse hepatocytes and cannot support significant transposon expression over time in the absence of stable genomic integration. Analysis of liver sections obtained two days after vector administration showed reporter gene expression in approximately 25% of mouse hepatocytes, consistent with efficient in vivo gene delivery to the liver (n=3 mice). When we analyzed reporter gene expression 6 weeks later, we found that gene expression persisted in 2.0±1% of mouse hepatocytes in the presence of the wild-type transposase (n=5) compared with just 0.06% in control mice that received no transposase (FIG. 16, left panel, n=5). These results are consistent with our previous work demonstrating transposase-mediated transgene integration into mouse chromosomes. More importantly, we observed approximately 5-fold more X-gal-positive mouse hepatocytes in animals expressing the K13A/K33A/T83A mutant transposase (9.3±3.0%, n=3) compared with wild-type SB-expressing mice (FIG. 16, left panel, right lane). This data suggests that an average of 37% of in vivo transfected mouse hepatocytes underwent a transposition event in the presence of the hyperactive mutant transposase.

We also produced a transposon encoding the serum marker protein human coagulation factor IX (hFIX)(FIG. 16, right panel) and studied its long-term persistence in vivo following co-delivery with wild-type or hyperactive transposase to the livers of immune-competent C57Bl/6 mice. Results demonstrate that the hyperactive transposase mutant HSB-3 can support ~7-fold more serum hFIX for more than 3 months (955 ng/ml±241 ng/ml) compared with mice expressing the wild-type (140 ng/ml±56 ng/ml), and 318-fold more FIX compared to mice that received no transposase (3 ng/ml±3 ng/m)(FIG. 16, right panel). This level of serum hFIX obtained with the improved transposase is ~19% of normal human levels, and is well within a curative range capable of converting a severely affected hemophilia B patient to one with a much milder phenotype. Accordingly, the results show that the improved activity of the hyperactive transposase mutants identified in mammalian cell culture systems is also applicable in vivo.

It is evident from the above results and discussion that the subject invention provides an important new method for inserting nucleic acids into the genomes of cells of multicellular organisms. Use of the enhanced Sleeping Beauty transposase system according to the subject methods provides for the ability to achieve stable integration of the a nucleic acid into the genome of one or more target cells and can be employed in a number of diverse applications. As such, the subject methods have wide ranging application, including in the field of gene therapy. Accordingly, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of integrating an exogenous nucleic acid into a genome of at least one vertebrate cell, said method comprising:
introducing into said vertebrate cell:
(a) a Sleeping Beauty transposon comprising said exogenous nucleic acid flanked by inverted repeats that are recognized by a Sleeping Beauty transposase; and
(b) a source of a mutant Sleeping Beauty transposase that provides for enhanced integration as compared to the Sleeping Beauty transposase of SEQ ID NO:01, wherein said mutant Sleeping Beauty transposase comprises one or more amino acid substitutions in amino acid residues selected from the group consisting of amino acid residues 13, 20, 29, 33, 34, 40, 49, 53, 55, 64, 69, 72, 83, 86, 88, 90, 91, 95, 96, 98, 103, 252, 254, 260, 270 and 277, in the amino acid sequence of SEQ ID NO:01;
so that said exogenous nucleic acid is integrated into said genome.

2. The method according to claim 1, wherein said source of a mutant Sleeping Beauty transposase comprises a nucleic acid encoding said mutant Sleeping Beauty transposase.

3. The method according to claim 1, wherein said transposon and said source of a mutant Sleeping Beauty transposase are present on separate vectors.

4. The method according to claim 1, wherein said transposon and said source of a mutant Sleeping Beauty transposase are present on the same vector.

5. The method according to claim 1, wherein said mutant Sleeping Beauty transposase comprises at least two amino acid substitutions.

6. The method according to claim 1, wherein said transposon comprises:
(a) an additional transposition enhancer; and
(b) an additional TA dinucleotide.

7. The method according to claim 6, wherein said additional transposition enhancer and said additional TA dinucleotide are present on the right terminus of said transposon.

8. The method according to claim 1, wherein said cell is present in vitro.

9. The method according to claim 1, wherein said cell is present in vivo.

10. The method according to claim 9, wherein said introducing comprises administering said transposon and the mutant Sleeping Beauty transposase to a vertebrate multicellular organism.

11. The method according to claim 10, wherein said vertebrate multicellular organism is a mammal.

12. The method according to claim 1, wherein said vertebrate cell is a mammalian cell.

13. The method according to claim 1, wherein said one or more amino acid substitutions are in amino acid residues selected from the group consisting of amino acid residues 252, 254, 260, 270 and 277, in the amino acid sequence of SEQ ID NO:01.

14. The method according to claim 1, wherein said one or more amino acid substitutions are in amino acid residue 254 and an amino acid residue selected from the group consisting of amino acid residues 252, 260, 270 and 277, in the amino acid sequence of SEQ ID NO:01.

15. The method according to claim 1, wherein said mutant Sleeping Beauty transposase has amino acid substitutions in amino acid residues 254 and 270 in the amino acid sequence of SEQ ID NO:01.

16. The method according to claim 1, wherein said one or more amino acid substitutions are in amino acid residues selected from the group consisting of amino acid residues 13, 33, 34, 64, 69, 72, 83, 90, 91 and 95, in the amino acid sequence of SEQ ID NO:01.

17. The method according to claim 1, wherein said one or more amino acid substitutions are in amino acid residue 33 and an amino acid residue selected from the group consisting of amino acid residues 13, 20, 29, 34, 40, 53, 55, 64, 69, 72, 83, 86, 88, 90, 91, 95, 96, 98 and 103, in the amino acid sequence of SEQ ID NO:01.

18. The method according to claim 1, wherein said one or more amino acid substitutions are in amino acid residue 33 and an amino acid residue selected from the group consisting of amino acid residues 13, 34, 64, 69, 72, 83, 90, 91 and 95, in the amino acid sequence of SEQ ID NO:01.

19. The method according to claim 1, wherein said one or more amino acid substitutions are in amino acid residue 33 and an amino acid residue selected from the group consisting of amino acid residues 13, 64, 69, 72, 83, 90, 91 and 95, in the amino acid sequence of SEQ ID NO:01.

20. The method according to claim 1, wherein said one or more amino acid substitutions are in amino acid residues 13, 33 and an amino acid residue selected from the group consisting of amino acid residues 83, 90 and 91, in the amino acid sequence of SEQ ID NO:01.

21. The method according to claim 1, wherein said one or more amino acid substitutions are in amino acid residues 13, 33, 83, 90 and 91 in the amino acid sequence of SEQ ID NO:01.

22. The method according to claim 1, wherein said mutant Sleeping Beauty transposase has a total number of amino acid substitutions that does not exceed 5 amino acid residues.

23. A transposon system comprising:
(a) a Sleeping Beauty transposon comprising an exogenous nucleic acid flanked by inverted repeats that are recognized by a Sleeping Beauty transposase; and
(b) a source of a mutant Sleeping Beauty transposase that provides for enhanced integration as compared to the Sleeping Beauty transposase of SEQ ID NO:01, wherein said mutant Sleeping Beauty transposase comprises one or more amino acid substitutions in amino acid residues selected from the group consisting of amino acid residues 13, 20, 29, 33, 34, 40, 49, 53, 55, 64, 69, 72, 83, 86, 88, 90, 91, 95, 96, 98, 103, 252, 254, 260, 270 and 277, in the amino acid sequence of SEQ ID NO:01.

24. A kit comprising:
(a) a Sleeping Beauty transposon comprising an exogenous nucleic acid flanked by inverted repeats that are recognized by a Sleeping Beauty transposase; and
(b) a source of a mutant Sleeping Beauty transposase that provides for enhanced integration as compared to the Sleeping Beauty transposase of SEQ ID NO:01, wherein said mutant Sleeping Beauty transposase comprises one or more amino acid substitutions in amino acid residues selected from the group consisting of amino acid residues 13, 20, 29, 33, 34, 40, 49, 53, 55, 64, 69, 72, 83, 86, 88, 90, 91, 95, 96, 98, 103, 252, 254, 260, 270 and 277, in the amino acid sequence of SEQ ID NO:01.

* * * * *

UNITED STATES PATENT AND TRADEMARK OFFICE
CERTIFICATE OF CORRECTION

| | | |
|---|---|---|
| PATENT NO. | : 7,985,739 B2 | Page 1 of 1 |
| APPLICATION NO. | : 10/861108 | |
| DATED | : July 26, 2011 | |
| INVENTOR(S) | : Kay et al. | |

It is certified that error appears in the above-identified patent and that said Letters Patent is hereby corrected as shown below:

In the Specification Under Column 1:

• Please replace Column 1, line no. 13-18 with:

-- FEDERALLY-SPONSORED RESEARCH OR DEVELOPMENT
This invention was made with Government support under contracts DK049022 & AR044012 awarded by the National Institutes of Health. The Government has certain rights in this invention. --

Signed and Sealed this
Twenty-eighth Day of May, 2013

Teresa Stanek Rea
*Acting Director of the United States Patent and Trademark Office*